(12) United States Patent
Benton et al.

(10) Patent No.: US 6,514,746 B1
(45) Date of Patent: Feb. 4, 2003

(54) STAPHYLOCOCCUS AUREUS HISTIDINE PROTEIN KINASE ESSENTIAL GENES

(75) Inventors: Bret Benton, San Bruno, CA (US); Francois Malouin, Los Gatos, CA (US); Patrick K. Martin, Sunnyvale, CA (US); Molly B. Schmid, Los Altos, CA (US); Dongxu Sun, Cupertino, CA (US)

(73) Assignee: Essential Therapeutics, Inc., Mountain View, CA (US)

( * ) Notice: Subject to any disclaimer, the term of this patent is extended or adjusted under 35 U.S.C. 154(b) by 0 days.

(21) Appl. No.: 09/082,077

(22) Filed: May 20, 1998

Related U.S. Application Data

(63) Continuation-in-part of application No. PCT/US97/23912, filed on Dec. 23, 1997, and a continuation-in-part of application No. 08/713,718, filed on Sep. 13, 1996.
(60) Provisional application No. 60/003,798, filed on Sep. 15, 1995, and provisional application No. 60/009,102, filed on Dec. 22, 1995.

(51) Int. Cl.$^7$ ................................................ C12N 1/20
(52) U.S. Cl. .................. 435/252.3; 536/23.1; 536/24.3; 536/24.32; 536/24.33; 435/320.1
(58) Field of Search .............................. 536/23.1, 23.2, 536/23.7, 24.3, 24.32, 24.33; 435/252.3, 320.1

(56) References Cited

U.S. PATENT DOCUMENTS

| | | |
|---|---|---|
| 5,246,838 A | 9/1993 | Van Dijl et al. ........... 435/69.1 |
| 5,306,619 A | 4/1994 | Edwards et al. ............... 435/6 |

FOREIGN PATENT DOCUMENTS

| | | |
|---|---|---|
| EP | 0 786 519 A2 | 7/1997 |
| WO | 96/23075 | 8/1996 |
| WO | 97/11690 | 4/1997 |

OTHER PUBLICATIONS

Green et al. (Sep. 20, 1993) Genbank Accession No. L11530. Accessed Jun. 12, 2000.*
Welsh et al. (May 13, 1992) GenBank Accession No. X66088. Accessed Jun. 12, 2000.*
Abdelnour et al., "The Accessory Gene Regulator (arg) Controls *Staphylococcus aureus* Virulence in a Murine Arthritis Model," *Infection and Immunity* 61:3879–3885 (1993).
Alber, "Mutational Effects on Protein Stability," *Ann. Rev. Biochem.* 58:765–798 (1989).
Altschul et al., "Basic Local Alignment Search Tool," *J. Mol. Biol.* 215:403–410 (1990).
Anderson and Roth, "Tandem Genetic Duplications in Phage and Bacteria," *Ann. Rev. Biochem.* 31:473–505 (1977).

Arvidson et al., "Ch. 30—The Role of the δ–Lysin Gene (hld) in the agr–Dependent Regulation of Exoprotein Synthesis in *Staphylococcus aureus*," *Molecular Biology of the Satphylococci*, R.P. Novick, ed., VCH, New York, New York, pp. 419–431 (1990).
Bannatyne et al., "Comparison of the Efficacy of Cilofungin, Fluconazole and Amphotericin B in the Treatment of Systemic *Candida albicans* Infection in the Neutropenic Mouse," *Infection* 20:168–171 (1992).
Berger–Bachi et al., "FemA, a host–mediated factor essential for methicillin resistance in *Staphylococcus auerus*: Molecular cloning and characterization," *Mol. Gen. Genet.* 219:263–269 (1989).
Bergeron, "A Review of Models for thr Therapy of Experimental Infections," *Scand. J. Infect Dis. Suppl.* 14:189–206 (1978).
Borodovsky et al., "Intrinsic and Extrinsic Approaches for Detecting Genes in a Bacteriol Genome," *Nucl. Acids Res.* 22:4756–4767 (1994).
Camilli et al., "Insertional Mutagenesis of Listeria Monocytogenes with a Novel Tn917 Derivative That Allows Direct Cloning of DNA Flaking Transposon Insertions," *J. Bacteriol.* 172:3738–3744 (1990).
Chow and Wong, "Cloning and Nucleotide Sequence of the structural gene coding for *Bacillus subtilis* tryptophanyl tRNA synthetase," *Gene* 73:537–543 (1988).
Davis, "Activity of Gentamicin, Tobramycin, Polymyxin B, and Colistimenthate in Mouse Protection Tests with *Pseudomonas aeruginosa*," *Antimicrobial Agents and Chemotherapy* 8:50–53 (1975).
Day et al., "A simple method for the study in vivo of bacterial growth and accompanying host response," *Journal of Infection* 2:39–51 (1980).
Falkow et al., "The Interaction of Bacteria with Mammalian Cells," *Ann. Rev. Cell. Biol.* 8:333–363 (1992).

(List continued on next page.)

Primary Examiner—Sean McGarry
Assistant Examiner—Janet L. Epps
(74) Attorney, Agent, or Firm—Bernard F. Rose; Bingham McCutchen LLP

(57) ABSTRACT

This disclosure describes isolated or purified deoxyribonucleotide (DNA) sequences, useful for the development of antibacterial agents, which contain the coding sequences of bacterial genes which encode the components of a two-component regulatory pair. It further describes isolated or purified DNA sequences which are portions of such bacterial genes, which are useful as probes to identify the presence of the corresponding gene or the presence of a bacteria containing that gene. Also described are hypersensitive mutant cells containing a mutant gene corresponding to any of the identified sequences and methods of screening for antibacterial agents using such hypersensitive cells. In addition it describes methods of treating bacterial infections by administering an antibacterial agent active against one of the identified targets, as well as pharmaceutical compositions effective in such treatments.

6 Claims, 11 Drawing Sheets

OTHER PUBLICATIONS

Fingl and Woodbury, "Chapter 1—General Principles," in *The Pharmacological Basis of Therapeutics*, 5th edition, Goodman and Gilman editors, MacMillan Publishing Co., Inc., New York, pp. 1–46 (1975).

Gordee et al., "In Vitro and In Vivo Anti–Candida Activity and Toxicology of LY121019," *J. Antibiotics* 37:1054–1065 (1984).

Hamill et al., "Phagocytosis of *Staphylococcus aureus* by Culture Bovine Aortic Endothelial Cells: Model for Postadherence Events in Endovascular Infections," *Infection and Immunity* 54:833–836 (1986).

Hecht et al., "Mutations in λ repressor's amino–terminal domain: Implications for protein stability and DNA binding," *Proc. Natl. Acad. Sci. USA* 80:2676–2680 (1983).

Hong and Ames, "Localized Mutagenesis of any specific Small Region of the Bacterial Chromosome," *Proc. Natl. Acad. Sci. USA* 68:3158–3162 (1971).

Horinouchi and Weisblum, "Nucleotide Sequence and Functional Map of pE194, a Plasmid That Specifies Inducible Resistance to Macrolide, Lincosamide, and Streptogramin Type B Antibiotics," *J. Bacteriology* 150:804–814 (1982).

Iordanescu and Bargonetti, "*Staphylococcus aureus* Chromosomal Mutations That Decrease Effiency of Rep Utilization in Replication of pT181 and Related Plasmids," *Journal of Bacteriology* 171:4501–4503 (1989).

Ishino et al., "Nucleotide sequence of the lig gene and primary structure of Dna ligase of *Escherichia coli*," *Mol. Gen. Genet.* 204:1–7 (1986).

Joshi and Singh, "Potential organofluorine oral hypoglycemic agents," *J. Prakt. Chem.* 313(1):169–173 (1971).

Kamogashira and Takegata, "A Screening Method for Cell Wall Inhibitors Using a D–Cycloserine Hypersensitive Mutant," *J. Antibiotics* 41:803–806 (1988).

Kelly et al., "Surface Characteristics of *Pseudomonas aeruginosa* Grown in a Chamber Implant Model in Mice and Rats," *Infection and Immunity* 57:344–350 (1989).

Lee, et al., "Characterization of the Genes and Proteins of a Two–Component System for the Hyperthermophilic Bacterium Thermotoga Maritima," *J. Bacteriol.* 178:5579–5585 (1996).

Malouin et al., "Outer Membrane and Porin Characteristics of *Serratia marcescens* Grown In Vitro and in Rat Intraperitoneal Diffusion Chambers," *Infection and Immunity* 58:1247–1253 (1990).

Moriya et al., "Structure and function of the region of the replication origin of the *Bacillus subtilis* chromosome. III. Nucleotide sequence of some 10,000 base pairs in the origin region," *Nucleic Acids Research* 13:2251–2265 (1985).

Murray, "Can Antibiotic Resistance be Controlled?" *New England J. Med.* 330:1229–1230 (1994).

Normark et al., "*Escherichia coli* K–12 Mutants Hyperproducing Chromosomal Beta–Lactamase by Gene Repetitions," *J. Bacteriology* 132:912–922 (1977).

Numata et al., "Isolation of an Aminoglycoside Hypersensitive Mutant and its Application in Screening," *J. Antibiotics* 39:994–1000 (1986).

Ogasawara, et al., "Systematic Sequencing of the 180 Kilobase Region of the *Bacillus Subtilis* Chromosome Containing the Replication Origin," *DNA Res.* 1:1–4 (1994).

Ogawa et al., "Bacterial Adherence to Human Endothelial Cells In Vitro," *Infection and Immunity*, 50:218–224 (1985).

Pachamia et al., "Studies on 2,5–Disubsituted–1,3,4–oxadiazoles. Part II. Preparation and Antimicrobial Activity of 2–Arylsulphonamido/a–carbamylarymethylamino–5–(4–pyridyl)–1,3,4–oxadiazoles," *J. Indian Chem. Soc.* 65(5):357–361 (1988).

Pattee, "*Staphylococcus Aureus*," in *Genetic Maps: Locus Maps of Complex Genomes*, 5th edition, edited by Stephen J. O'Brien, Cold Spring Harbor Laboratory Press, 2.22–2.27 (1990).

Pattee, "Ch.11—Genetic and Physical Mapping of the Chromosome of *Staphylococcus aureus* NCTC 8325," *The Bacterial Chromosome*, edited by drlic and Riley, American Society for Microbiology, Washington, D.C., pp. 163–169 (1990).

Pearson and Lipman, "Improved tools for biological sequence comparison," *Proc. Natl. Acad. Sci. USA* 85:2444–2448 (1988).

Sanger et al., "DNA sequencing with chain–terminating inhibitors," *Proc. Natl. Acad. Sci. USA* 74:5463–5467 (1977).

Santoro and Levison, "Rat Model of Experimental Endocarditis," *Infection and Immunity* 19:915–918 (1978).

Schmid et al., "Genetic Analysis of Temperature–Sensitive Lethal Mutants of *Salmonella typhimurium,*" *Genetics* 123:625–633 (1989).

Seki, et al., "Cloning and Nucleotide Sequence of phoP, the Regulatory Gene for Alkaline Phosphatase and Phosphodiesterase in *Bacillus Subtilis,*" *J. Bacteriol.* 169:213–2916 (1987).

Spagnolo et al., "Chronic *Staphylococcal Osteomyelitis*: a New Experimental Rat Model," *Infection and Immunity* 61:5225–5230 (1993).

Stark and Wahl, "Gene Amplification," *Ann. Rev. Biochem.* 53:447–491 (1984).

Sun, et al., "Regulators of Aerobic and Anaerobic Respiration in *Bacillus Subtilis*," *J. Bacteriol.* 178:1374–1385 (1996).

Tokunaga et al., "Isolation and Characterization of an *Escherichia coli* Clone Overproducing Prolipoprotein Signal Peptidase," *J. Biol. Chem.* 258:12102–12105 (1983).

Vann and Proctor, "Cytotoxic effects of ingested *Staphylococcus aureus* on bovine endothelial cells:: Role of *S. aureus* a–hemolysin," *Microbial Pathogenesis* 4:443–453 (1988).

Vogelman et al., "In Vivo Postantibiotic Effect in a Thigh Infection in Neutropenic Mice," *Journal of Infectious Diseases* 157:287–298 (1988).

Volz, *Biochemistry* 332:11741–11753 (1993).

Yanisch–Perron, "Improved M13 phage cloning vectors and host strains: nucleotide sequences of the M13mp and pUC19 vectors," *Gene* 33:103–119 (1985).

* cited by examiner

```
SEQ ID NO. 1
SEQ ID NO. 2
SEQ ID NO. 3

GATCGCGGGTTCGATTCCCGTCGAGACCGTACAAATGCCTATCCAAGAGGATAGCCATTTTTTTGCGTTTAATATTATAT
----+----+----+----+----+----+----+----+----+----+----+----+----+----+----+----+   80

TAATAAAAGATATGGACGAATGATAATCATATTGATTTATCTGTTCGTCCATTTCTTTAAAATGTATGAACCTCAAG
----+----+----+----+----+----+----+----+----+----+----+----+----+----+----+----+   160

TAACTTAGTGGTTGGATATGAAAGATAAACGTAGACAATAAAATCTTTATTAGACGTACAAACATATGCTACTGTCAACA
----+----+----+----+----+----+----+----+----+----+----+----+----+----+----+----+   240

TATTTCTTCGTTGTGATATGCCACCAGTCCTCCATAACATCAATTGTTAAAGTAACGAATAACGAATAATGATATTTATT
----+----+----+----+----+----+----+----+----+----+----+----+----+----+----+----+   320

TTCTGAGCAATGACGTGCAACTAGAAGTTGCCATTATCCTAATTTTATTATTGGAATAGAGACCTCATCATTGTGTTAAA
----+----+----+----+----+----+----+----+----+----+----+----+----+----+----+----+   400

TATCATTGTCACAATCCGCCGTGAGAAACTAATAAAAAATAGTAATATAAGTTTATATTGGAAAATAGAATTAATAGC
----+----+----+----+----+----+----+----+----+----+----+----+----+----+----+----+   480

TTATAAATGGTAAATTATATAATAGGTTACTATACGTTATAAGACGGAAAATGCGCACAATAACAAAAATAGTAAGCGAC
----+----+----+----+----+----+----+----+----+----+----+----+----+----+----+----+   560

ATCCTGTGATTTTTTACACAAACATAAACGATAAAGAACAAAAAATGATAAAATAATTAATGATTAAGAAAAGAGGT
----+----+----+----+----+----+----+----+----+----+----+----+----+----+----+----+   640

TTATGCAAATGGCTAGAAAAGTTGTTGTAGTTGATGATGAAAACCGATTGCTGATATTTAGAATTAACTTAAAAAAAA
----+----+----+----+----+----+----+----+----+----+----+----+----+----+----+----+   720
       M  A  R  K  V  V  V  V  D  D  E  K  P  I  A  D  I  L  E  F  N  L  K  K
```

Fig. 2A-1

```
GAAGGATACGATGTGTACTGTGCATACGATGGTAATGATGCAGTCGACTTAATTTATGAAGAAGAACCAGACATCGTATT     800
------+---------+---------+---------+---------+---------+---------+---------+
 E  G  Y  D  V  Y  C  A  Y  D  G  N  D  A  V  D  L  I  Y  E  E  E  P  D  I  V  L

ACTAGATATCATGTTACCTGGTCGTGATGGTATGGAAGTATGTCGTGAAGTGCGCAAAAATACGAAATGCCAATAATAA      880
------+---------+---------+---------+---------+---------+---------+---------+
 L  D  I  M  L  P  G  R  D  G  M  E  V  C  R  E  V  R  K  K  Y  E  M  P  I  I  M

TGCTTACTGCTAAAGATTCAGAAATTGATAAAGTGCTTGGTTTAGAACTAGGTGCAGATGACTATGTAACGAAACCGTTT     960
------+---------+---------+---------+---------+---------+---------+---------+
 L  T  A  K  D  S  E  I  D  K  V  L  G  L  E  L  G  A  D  D  Y  V  T  K  P  F

AGTACGCGTGAATTAATCGCACGTGTGAAAGCGAACTTACGTCGTCATTACTCACAACCAGCACAAGACACTGGAAATGT    1040
------+---------+---------+---------+---------+---------+---------+---------+
 S  T  R  E  L  I  A  R  V  K  A  N  L  R  R  H  Y  S  Q  P  A  Q  D  T  G  N  V

AACGAATGAAATCACAATTAAAGATATTGTGATTTATCCAGACGCATATTCTATTAAAAAACGTGGCGAAGATATTGAAT    1120
------+---------+---------+---------+---------+---------+---------+---------+
 T  N  E  I  T  I  K  D  I  V  I  Y  P  D  A  Y  S  I  K  K  R  G  E  D  I  E  L

TAACACCATCGTGAATTTGAATTGTTCCATTATTTATCAAAACATATGGGACAAGTAATGACACGTGAACATTTATTACAA   1200
------+---------+---------+---------+---------+---------+---------+---------+
 T  H  R  E  F  E  L  F  H  Y  L  S  K  H  M  G  Q  V  M  T  R  E  H  L  L  Q
```

Fig. 2A-2

```
ACAGTATGGGGCTATGATTACTTTGGGCGATGTACGGTCGATGTAACGATTCGTCGTTTACGTGAAAAGATTGAAGA      1280
---+---------+---------+---------+---------+---------+---------+---------+---
 T  V  W  G  Y  D  Y  F  G  D  V  R  T  V  D  V  T  I  R  R  L  R  E  K  I  E  D

TGATCCGTCACATCCTGAATATATTGTGACGCGTTGGATATTCCTCCAACAACATGAGTAGAGGTCGAAAC         1360
---+---------+---------+---------+---------+---------+---------+---------+---
 D  P  S  H  P  E  Y  I  V  T  R  R  G  V  G  Y  F  L  Q  Q  H  E  *

GAATGAAGTGGCTAAAACAACTACAATCCCTTCATACTAAACTTGTAATTGTTTATGTATTACTGATTATCATTGGTATG  1440
---+---------+---------+---------+---------+---------+---------+---------+---
 M  K  W  L  K  Q  L  Q  S  L  H  T  K  L  V  I  V  Y  V  L  L  I  I  G  M

CAAATTATCGGGTTATATTTTACAAATAACCTTGAAAAAGAGCTGCTTGATAATTTTAAGAAGAATATTACGCAGTACGC  1520
---+---------+---------+---------+---------+---------+---------+---------+---
 Q  I  I  G  L  Y  F  T  N  N  L  E  K  E  L  L  D  N  F  K  K  N  I  T  Q  Y  A

GAAACAATTAGAAATTAGTATTGAAAAGTATATGACGAAAAAGGGCTCCGTAAATGCACAAAAAGATATTCAAAATTTAT  1600
---+---------+---------+---------+---------+---------+---------+---------+---
 K  Q  L  E  I  S  I  E  K  V  Y  D  E  K  G  S  V  N  A  Q  K  D  I  Q  N  L  L

TAAGTGAGTATGCCAACCGTCAAGAAATTCGTTTTATAGATAAAGACCAAATTATTGCGACGACGAAG            1680
---+---------+---------+---------+---------+---------+---------+---------+---
 S  E  Y  A  N  R  Q  E  I  G  E  I  R  F  I  D  K  D  Q  I  I  A  T  T  K

CAGTCTAACCGTAGTCTAATCAATCAAAAAGCGAATGATAGTTCTGTCCAAAAAGCACTATCACTAGGACAATCAAACGA  1760
---+---------+---------+---------+---------+---------+---------+---------+---
 Q  S  N  R  S  L  I  N  Q  K  A  N  D  S  S  V  Q  K  A  L  S  L  G  Q  S  N  D

TCATTAATTTAAAAGATTATGGCGGTGGTAAGGACCGTGTCTGGGTATATATCCCAGTTAAAGTCGATAAAAAGG      1840
---+---------+---------+---------+---------+---------+---------+---------+---
 H  L  I  L  K  D  Y  G  G  G  K  D  R  V  W  V  Y  N  I  P  V  K  V  D  K  K  V
```

Fig. 2A-3

```
TAATTGGTAATATTTATATCGAATCAAAAATTAATGACGTTTATAACCAATTAAATAATAAATCAAATATTCATTGTT
----------+---------+---------+---------+---------+---------+---------+---------+    1920
  I  G  N  I  Y  I  E  S  K  I  N  D  V  Y  N  Q  L  N  N  I  N  Q  I  F  I  V

GGTACAGCTATTCATTATTAATCACAGTCATCCTCTAGGATTCTTTATAGCGAACGATTACCAAACCAATCACCGATAT
----------+---------+---------+---------+---------+---------+---------+---------+    2000
  G  T  A  I  S  L  L  I  T  V  I  L  G  F  F  I  A  R  T  I  T  K  P  I  T  D  M

GCGTAACCAGACGGTCGAAATGTCCAGAGTAACTATACGCAACGTGTGAAGATTTATGGTAATGATGAAATTGGCGAAT
----------+---------+---------+---------+---------+---------+---------+---------+    2080
  R  N  Q  T  V  E  M  S  R  G  N  Y  T  Q  R  V  K  I  Y  G  N  D  E  I  G  E  L

TAGCTTTAGCATTTAATAACTTGTCTAAACGTGTACAAGAAGCCAGGCTAATACTGAAAGTGAGAAACGTAGACTGGAC
----------+---------+---------+---------+---------+---------+---------+---------+    2160
  A  L  A  F  N  N  L  S  K  R  V  Q  E  A  Q  A  N  T  E  S  E  K  R  R  L  D

TCAGTTATCACCCATATGAGTGATGGTATTATTGCAACAGACCGCCGTGGACGTATTCGTATCGTCAATGATATGGCACT
----------+---------+---------+---------+---------+---------+---------+---------+    2240
  S  V  I  T  H  M  S  D  G  I  I  A  T  D  R  R  G  R  I  R  I  V  N  D  M  A  L

CAAGATGCTTGGTATGGCGAAAGAAGAAGACATCATCGGATATATTACATGTTAAGTGTATTAAGTCTTGAAGATGAATTTAAAC
----------+---------+---------+---------+---------+---------+---------+---------+    2320
  K  M  L  G  M  A  K  E  D  I  I  G  Y  Y  M  L  S  V  L  S  L  E  D  E  F  K  L

TGGAAGAAATTCAAGAGAATAATGATAGTTTCTTATTAGATTTAAATGAAGAAGAAGGTCTAATCGCACGTGTTAACTTT
----------+---------+---------+---------+---------+---------+---------+---------+    2400
  E  E  I  Q  E  N  N  D  S  F  L  L  D  L  N  E  E  E  G  L  I  A  R  V  N  F
```

*Fig. 2A-4*

```
AGTACGATTGTGCAGGAAACAGGATTGTAACTGGTTATATCGCTGTGTTACATGACGTAACTGAACAACAACAAGTTGA
  -----+---------+---------+---------+---------+---------+---------+---------+   2480
  S  T  I  V  Q  E  T  G  F  V  T  G  Y  I  A  V  L  H  D  V  T  E  Q  Q  V  E

ACGTGAGCGTCGTGAATTTGTTGCCAATGTATCACATGAGTTACGTACACCTTTAACTTCTATGAATAGTTACATTGAAG
  -----+---------+---------+---------+---------+---------+---------+---------+   2560
  R  E  R  R  E  F  V  A  N  V  S  H  E  L  R  T  P  L  T  S  M  N  S  Y  I  E  A

CACTTGAAGAAGGTGCATGGAAAGATGAGGAACTTGCGCCACAATTTTATCTGTTACCCGTGAAGAAACAGAACGAATG
  -----+---------+---------+---------+---------+---------+---------+---------+   2640
  L  E  E  G  A  W  K  D  E  E  L  A  P  Q  F  L  S  V  T  R  E  E  T  E  R  M

ATTCGACTGGTCAATGACTTGCTACAGTTATCTAAAATGGATAAGAGTCTGATCAAATCAACAAAGAAATTATCGACTT
  -----+---------+---------+---------+---------+---------+---------+---------+   2720
  I  R  L  V  N  D  L  L  Q  L  S  K  M  D  N  E  S  D  Q  I  N  K  E  I  I  D  F

TAACATGTTCATTAATAAAATTATTAATCGACATGAAAATGTCTCGCGAAAGATACAACATTTATTCGAGATATTCCGAAAA
  -----+---------+---------+---------+---------+---------+---------+---------+   2800
  N  M  F  I  N  K  I  I  N  R  H  E  M  S  A  K  D  T  T  F  I  R  D  I  P  K

AGACGATTTTCACAGAATTTGATCCTGATAAAATGACGCAAGTATTTGATAATGTCATTACAAATGCGATGAAATATTCT
  -----+---------+---------+---------+---------+---------+---------+---------+   2880
  T  I  F  T  E  F  D  P  D  K  M  T  Q  V  F  D  N  V  I  T  N  A  M  K  Y  S

AGAGGGCGATAAACGTGTCGAGTTCCACGTGAAAACAAATCCACTTTATAATCGAATGACGATTCGTATTAAGATAATGG
  -----+---------+---------+---------+---------+---------+---------+---------+   2960
  R  G  D  K  R  V  E  F  H  V  K  Q  N  P  L  Y  N  R  M  T  I  R  I  K  D  N  G

CATTGGTATTCCTATCAATAAAGTCGATAAGATATTCGACCGATTCTATCGTGATAAGGCACGTACGCGTAAAATGG
  -----+---------+---------+---------+---------+---------+---------+---------+   3040
  I  G  I  P  I  N  K  V  D  K  I  F  D  R  R  F  Y  R  V  D  K  A  R  T  R  K  M  G
```

*Fig. 2A-5*

```
GTGGTACTGGATTAGGACTAGCCATTTCGAAAGAGATTGTGGAAGCGCACAATGGTCGTATTTGGGCAAACAGTGTAGAA   3120
------+---------+---------+---------+---------+---------+---------+---------+
 G  T  G  L  G  L  A  I  S  K  E  I  V  E  A  H  N  G  R  I  W  A  N  S  V  E

GGTCAAGGTACACATCTATCTTTATCACACTTCCATGTGAAGTCATTGAAGACGGTGATGAATAATAAGGAGCATA        3200
------+---------+---------+---------+---------+---------+---------+---------+
 G  Q  G  T  S  I  F  I  T  L  P  C  E  V  I  E  D  G  D  W  D  E  *

TTAAATCTGTCATTTTAGCACTACTCGTCTCGTCTTGATGAGTGTGCGTATTGACATATATGGTATGGAACTTTTCTCCTGATATT   3280
------+---------+---------+---------+---------+---------+---------+---------+

GCAAATGTCGACAATACAGATAGTAAGAAGAGTGAAACGAAACCTTTAACGACACCTATGACAGCCAAAATGGATACAAC        3360
------+---------+---------+---------+---------+---------+---------+---------+

TATTACGCCATTTCAGATTATTCATTCGAAAAAATGATCATCCAGAAGGAACGATTGCGACGGTATCTAATGTGAATAAAC        3440
------+---------+---------+---------+---------+---------+---------+---------+

TGACGAAACCTTTGAAAAAATAAAGAAGTGAAGTCCGTGGAACATGTTCGTCGTGATCATAACTTGATGATTCCTGATTTG       3520
------+---------+---------+---------+---------+---------+---------+---------+

AACAGTGATTTTATATTATTCGATTTTACGTATGATTTACCGTTATCAACATATCTTGGTCAAGTACTGAACATGAATGC        3600
------+---------+---------+---------+---------+---------+---------+---------+

GAAAGTACCAAATCATTTCAATTTCAATCGTTTGGTCATAGATCTTGATGCTGATGATAATATCGTGCTTTATGCTATAA       3680
------+---------+---------+---------+---------+---------+---------+---------+

GCAAAGATCGCCACGATTACGTAAAAATTAACAACTACAACGAAAAATGATC   3731
------+---------+---------+---------+---------+---
```

Fig. 2A-6

```
         1
Sau_espA   MARKVVVVDD EKPIADILEF NLKKEGYDVY CAYDGNDAVD LIYEEEPDIV    50
Bsu_yycF   MDKKILVVDD EKPIADILEF NLRKEGYEVH CAHDGNEAVE MVEELQPDLI
Spy_yycF   .MKKILIVDD EKPISDIIKE NLTKEGYDIV TAFDGREAVT IFEEEKPDLI
Bsu_phoP   MNKKILVVDD EESIVTLLQY NLERSGYDVI TASDGEEALK KAETEKPDLI 51
Sau_espA   LLDIMLPGRD GMKVCREVR. KKYEMPIIML TGKDSEIDKV LGLELGADDY    100
Bsu_yycF   LLDIMLPNKD GVEVCREVR. KKYDMPIIML TAKDSEIDKV IGLEIGADDY
Spy_yycF   ILDIMLPELD GLEVAKEIR. KTSHVPIIML SAKDSEFDKV IGLEIGADDY
Bsu_phoP   VLDVMLPKLD GIEVCKQLRQ QKLMFPILML TAKDEEFDKV LGLELGADDY 101
Sau_espA   VTKPFSTREL IARVKANLRR ....HYSQPA QDTGNVTNEI TIKDIVIYPD    150
Bsu_yycF   VTKPFSTREL LARVKANLRR ....QLTTAP AEEEPSSNEI HIGSLVIFPD
Spy_yycF   VTKPFSNREL LARVKAHLRR TETIETAVAE ENASSGTQEL TIGNLQILPD
Bsu_phoP   MTKPFSPREV NARVKAILRR SE.IRAPSSE MKNDEMEGQI VIGDLKILPD 151
Sau_espA   AYSIKKRGED IELTHREFEL FHYLSKHMGQ VMTREHLLQT VWGYDYFGDV    200
Bsu_yycF   AYVVSKRDET IELTHREFEL LHYLAKHIGQ VMTREHLLQT VWGYDYFGDV
Spy_yycF   AFVAKKHGQE VELTHREFEL LHHLANHMGQ VMTREHLLEI VWGYDYFGDV
Bsu_phoP   HYEAIFKESQ LELTPKEFEL LLYLGRHKGR VLTRDLLLSA VWNYDFAGDT 201                                                    243
Sau_espA   RTVDVTIRRL R.EKIEDDPS HPEYIVTRRG VGYFLQQHE
Bsu_yycF   RTVDVTVRRL R.EKIEDNPS HPNWIVTRRG VGYYLRNPEQ D
Spy_yycF   RTVDVTVRRL R.EKIEDTPS RPEYILTRRG VGYYMKSYD
Bsu_phoP   RIVDVHISHL RRTKIENNTK KPIYIKTIRG LGYKLEEPKM NE*
```

Fig. 3

HPK INHIBITORS-SCREENING

HEPA NP SCREEN – HIT VALIDATION

| | | % INHIBITION ON *Staphylococcus* AT VARIOUS CONCENTRATIONS OF EXTRACT CONCENTRATION (%) | | | | | | | | | | | |
|---|---|---|---|---|---|---|---|---|---|---|---|---|---|
| COMPOUND | MICROBE | 2 | 1 | 0.5 | 0.25 | 0.12 | 0.06 | 0.03 | 0.015 | 0.007 | 0.003 | 0.001 | 0.0009 |
| MXC005:E3 | 8325-4 | 92 | 79 | 88 | 36 | 17 | 4 | 12 | 10 | 5 | -3 | -13 | -17 |
| | NT372 | 102 | 95 | 96 | 100 | 96 | 98 | -9 | 3 | -7 | 4 | -3 | 3 |
| | SAM533 | 107 | 97 | 27 | 32 | -16 | 1 | 30 | -69 | -107 | -102 | -153 | 30 |

STAPHYLOCOCCUS AUREUS HISTIDINE PROTEIN KINASE ESSENTIAL GENES

This application is a continuation-in-part of Benton et al., PCT/US97/23912, filed Dec.23, 1997, entitled STAPHYLOCOCCUS AUREUS HISTIDINE PROTEIN KINASE ESSENTIAL GENES, and is a continuation-in-part of Benton et al., U.S. Ser. No. 08/713,718, entitled STAPHYLOCOCCUS AUREUS ANTIBACTERIAL TARGET GENES, filed Sep. 13, 1996, which claims the benefit of provisional application 60/003,798, filed Sep. 15, 1995, and provisional application 60/009,102, filed Dec. 22, 1995, which are incorporated herein by reference in their entireties, including drawings.

BACKGROUND

This invention relates to the field of antibacterial treatments and to targets for antibacterial agents. In particular, it relates to genes essential for survival of a bacterial strain in vitro or in vivo.

The following background information is not admitted to be prior art to the pending claims, but is provided only to aid the understanding of the reader.

Despite the development of numerous antibacterial agents, bacterial infections continue as a major, and currently increasing, medical problem. Prior to the 1980s, bacterial infections in developed countries could be readily treated with available antibiotics. However, during the 1980s and 1990s, antibiotic resistant bacterial strains emerged and have become a major therapeutic problem. There are, in fact, strains resistant to essentially all of the commonly used antibacterial agents, which have been observed in the clinical setting, notably including strains of *Staphylococcus aureus* (*S. aureus*) The consequences of the increase in resistant strains include higher morbidity and mortality, longer patient hospitalization, and an increase in treatment costs (B. Murray, 1994, New Engl. *J. Med.* 330:1229–1230). Therefore, there is a pressing need for the development of new antibacterial agents which are not significantly affected by the existing bacterial resistance mechanisms.

Such development of new antibacterial agents can proceed by a variety of methods, but generally fall into at least two categories. The first is the traditional approach of screening for antibacterial agents without concern for the specific target.

The second approach involves the identification of new targets, and the subsequent screening of compounds to find antibacterial agents affecting those targets. Such screening can involve any of a variety of methods, including screening for inhibitors of the expression of a gene, or of the product of a gene, or of a pathway requiring that product. However, generally the actual target is a protein, the inhibition of which prevents the growth or pathogenesis of the bacterium. Such protein targets can be identified by identifying genes encoding proteins essential for bacterial growth.

SUMMARY

Each pathogenic bacterial species expresses a number of different genes which are essential for growth of the bacteria in vitro or in vivo in an infection, and which are useful targets for antibacterial agents. This invention concerns the identification and use of particular essential genes and bacterial strains expressing mutant forms of those genes in the identification, characterization, and evaluation of antibacterial agents. Thus, this invention also provides methods of treating bacterial infections in mammals by administering an antibacterial agent active against such a gene, and the pharmaceutical compositions effective for such treatment.

For the *Staphylococcus aureus* essential genes identified in this invention, the essential nature of the genes was determined by the isolation of growth conditional mutants of *S. aureus*, in this case temperature sensitive mutants (ts mutants). Each gene was then identified by isolating recombinant bacteria derived from the growth conditional mutant strains, which would grow under non-permissive conditions but which were not revertants. These recombinant bacteria contained DNA inserts derived from the normal (i.e., wild-type) *S. aureus* chromosome which encoded non-mutant products which replaced the function of the products of the mutated genes. The fact that a clone having such a recombinant insert can complement the mutant gene product under non-permissive conditions implies that the insert contains essentially a complete gene, since it produces functional product.

The Staphylococcal genes described herein have been completely sequenced and analyzed. These two genes are named espA (SEQ ID NO. 2), encoding EspA, a polypeptide of the response regulator family (SEQ ID NO. 4), and espB (SEQ ID NO. 3), encoding EspB, a polypeptide of the histidine kinase family (SEQ ID NO. 5), respectively. These can be considered to be two separate genes or together to comprise one dicistronic gene.

In a first aspect, this invention provides a method of screening for an antibacterial agent by determining whether a test compound is active against one of the identified bacterial genes. These genes have been identified as essential genes by the isolation of a growth conditional mutant strain, and the complementation in recombinant strains of each of the genes, by expression from artificially-inserted DNA sequences carrying genes identified by the specified sequences of SEQ ID NO. 1–3.

In a particular embodiment the method is performed by providing a bacterial strain having a mutant form of a gene selected from the group of genes corresponding to SEQ. ID. NO. 1–3' or a mutant gene homologous to one of those genes. The mutant form of the gene confers a growth conditional phenotype, e.g., a temperature-sensitive phenotype, on the bacterial strain having that mutant form. A comparison bacterial strain having a normal form of the gene is also provided and the two strains of bacteria are each contacted with a test compound, preferably under semi-permissive growth conditions. The growth of the two strains in the presence of the test compound is then compared; a reduction in the growth of the bacterial strain having the mutant form compared to the growth of the bacterial strain having the normal form of the gene indicates that the test compound is active against the particular gene.

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "active against" in the context of compounds, agents, or compositions having antibacterial activity indicates that the compound exerts an effect on a particular bacterial target or targets which is deleterious to the in vitro and/or in vivo growth of a bacterium having that target or targets. In particular, a compound active against a bacterial gene exerts an action on a target which affects an expression product of that gene. This does not necessarily mean that the compound acts directly on the expression product of the gene, but instead indicates that the compound affects the expression product in a deleterious manner. Thus, the direct target of the compound may be, for example, at an upstream component which reduces transcription from the gene, resulting in a lower level of expression. Likewise, the compound may affect the level of translation of a polypeptide expression product, or may act on a downstream component of a biochemical pathway in which the expression product of the gene has a major biological role. Consequently, such a compound can be said to be active against the bacterial gene, against the bacterial gene product, or against the related component either upstream or downstream of that gene or expression product. While the term "active against" encompasses a range of potential activities, it also implies some degree of specificity of target. Therefore, for example, a general protease is not "active against" a particular bacterial gene which produces a polypeptide product. In contrast, a compound which specifically inhibits a particular enzyme is active against that enzyme and against the bacterial gene which codes for that enzyme.

The term "in vivo" in the context of a bacterial infection refers to the host infection environment, as distinguished, for example, from growth of the bacteria in an artificial culture medium (e.g., in vitro).

In the context of this disclosure, "bacterial gene" should be understood to refer to a unit of bacterial heredity as found in the chromosome of each bacterium. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the same way in referring to RNA chains, linear chains made of ribonucleotides.) The gene includes regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different bacterial strains, or even within a particular bacterial strain, without altering the identity of the gene.

Thus, "expressed bacterial gene" means that, in a bacterial cell of interest, the gene is transcribed to from RNA molecules. For those genes which are transcribed into mRNAs, the mRNA is translated to form polypeptides. More generally, in this context, "expressed" means that a gene product is formed at the biological level which would normally have the relevant biological activity (i.e., RNA or polypeptide level).

As used herein in referring to the relationship between a specified nucleotide sequence and a gene, the term "corresponds" or "corresponding" indicates that the specified sequence identifies the gene. Therefore, a sequence which will uniquely hybridize with a gene from the relevant bacterium corresponds to that gene (and the converse). In general, for this invention, the specified sequences have the same sequence (a low level of sequencing error or individual variation does not matter) as portions of the gene or flanking sequences. Similarly, correspondence is shown by a transcriptional, or reverse transcriptional relationship. Many genes can be transcribed to form mRNA molecules. Therefore, there is a correspondence between the entire DNA sequence of the gene and the mRNA which is, or might be, transcribed from that gene; the correspondence is also present for the reverse relationship, the messenger RNA corresponds with the DNA of the gene. This correspondence is not limited to the relationship between the full sequence of the gene and the full sequence of the mRNA, rather it also exists between a portion or portions of the DNA sequence of the gene and a portion or portions of the RNA sequence of the mRNA. Specifically it should be noted that this correspondence is present between a portion or portions of an mRNA which is not normally translated into polypeptide and all or a portion of the DNA sequence of the gene.

As used above and throughout this description of the invention, "hybridize" has its usual meaning from molecular biology. It refers to the formation of a base-paired interaction between nucleotide polymers. The presence of base pairing implies that at least an appreciable fraction of the nucleotides in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

Similarly, the DNA sequence of a gene or the RNA sequence of an mRNA "corresponds" to the polypeptide encoded by that gene and mRNA. This correspondence between the mRNA and the polypeptide is established through the translational relationship; the nucleotide sequence of the mRNA is translated into the amino acid sequence of the polypeptide. Then, due to the transcription relationship between the DNA of the gene and the mRNA, there is a "correspondence" between the DNA and the polypeptide.

The term, "bacterial gene product" or "expression product" is used to refer to a polypeptide or RNA molecule which is encoded in a DNA sequence according to the usual transcription and translation rules, which is normally expressed by a bacterium. Thus, the term does not refer to the translation of a DNA sequence which is not normally translated in a bacterial cell. However, it should be understood that the term does include the translation product of a portion of a complete coding sequence and the translation product of a sequence which combines a sequence which is normally translated in bacterial cells translationally linked with another DNA sequence. The gene product can be derived from chromosomal or extrachromosomal DNA, or even produced in an in vitro reaction. Thus, as used herein, an "expression product" is a product with a relevant biological activity resulting from the transcription, and usually also translation, of a bacterial gene.

A DNA containing a specific bacterial gene is obtainable using a shorter, unique probe(s) with readily available molecular biology techniques. If the method for obtaining such gene is properly performed, it is virtually certain that a longer DNA sequence comprising the desired sequence (such as the full coding sequence or the full length gene sequence) will be obtained. Thus, "obtainable by" means that an isolation process will, with high probability (preferably at least 90%, more preferably at least 95%), produce a DNA sequence which includes the desired sequence. Thus, for example, a full coding sequence is obtainable by hybridizing the DNA of two PCR primers appropriately derived from the sequences of SEQ ID No. 1–3 corresponding to a particular complementing clone to a *Staphylococcus aureus* chromosome, amplifying the sequence between the primers, and purifying the PCR products. The PCR products can then be used for sequencing the entire gene or for other manipulations. Those skilled in the art will understand the included steps, techniques, and conditions for such processes. However, the full coding sequence or full gene is clearly not limited to a specific process by which the sequence is obtainable. Such a process is only one method of producing the final product.

In this context, a "mutant form" of a gene is a gene which has been altered, either naturally or artificially, changing the base sequence of the gene, which results in a change in the amino acid sequence of an encoded polypeptide. The change in the base sequence may be of several different types, including changes of one or more bases for different bases, small deletions, and small insertions. By contrast, a normal form of a gene is a form commonly found in a natural population of a bacterial strain. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the bacterial strain having that gene, while a mutant form of a gene suitable for use in these methods does provide such a growth conditional phenotype.

As used in this disclosure, the term "growth conditional phenotype" indicates that a bacterial strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a bacterial strain having a heat-sensitive phenotype) exhibits significantly reduced growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes.

Thus, "semi-permissive conditions" are conditions in which the relevant culture parameter for a particular growth conditional phenotype is intermediate between permissive conditions and non-permissive conditions. Consequently, in semi-permissive conditions the bacteria having a growth conditional phenotype will exhibit growth rates intermediate between those shown in permissive conditions and non-permissive conditions. In general, such intermediate growth rate is due to a mutant cellular component which is partially functional under semi-permissive conditions, essentially fully functional under permissive conditions, and is non-functional or has very low function under non-permissive conditions, where the level of function of that component is related to the growth rate of the bacteria.

The term "method of screening" means that the method is suitable, and is typically used, for testing for a particular property or effect in a large number of compounds. Therefore, the method requires only a small amount of time for each compound tested; typically more than one compound is tested simultaneously (as in a 96-well microtiter plate), and preferably significant portions of the procedure can be automated. "Method of screening" also refers to determining a set of different properties or effects of one compound simultaneously. The preferred compounds are small molecules; preferably the molecular weight (MW) of the componds will be equal or less than 3,000 daltons, more preferably equal or less than 1,500 daltons, and even more preferably equal or less than 600 daltons.

Since the essential genes identified herein have been isolated and the gene products can be easily expressed by routine methods, the invention also provides the polypeptides encoded by those genes. Thus, the invention provides a method of screening for an antibacterial agent by determining the effects of a test compound on the amount or level of activity of a polypeptide gene product of one of the identified essential genes. The method involves contacting cells expressing such a polypeptide with a test compound, and determining whether the test compound alters the amount or level of activity of the expression product. The exact determination method will be expected to vary depending on the characteristics of the expression product. Such methods can include, for example, antibody binding methods, enzymatic activity determinations, and substrate analog binding assays.

It is quite common in identifying antibacterial agents, to assay for binding of a compound to a particular polypeptide where binding is an indication of a compound which is active to modulate the activity of the polypeptide. Thus, by identifying certain essential genes, this invention provides a method of screening for an antibacterial agent by contacting a polypeptide encoded by one of the identified essential genes, or a biologically active fragment of such a polypeptide, with a test compound, and determining whether the test compound binds to the polypeptide or polypeptide fragment.

In addition to simple binding determinations, the invention provides a method for identifying or evaluating an agent active on one of the identified essential genes. The method involves contacting a sample containing an expression product of one of the identified genes with the known or potential agent, and determining the amount or level of activity of the expression product in the sample.

In a related aspect, this invention provides an isolated or purified DNA sequence at least 15 nucleotides in length, preferably 20, 30, 50, 100, or more nucleotides, which has a nucleotide base sequence which is the same as or complementary to a portion of a bacterial gene selected from the group of genes corresponding to SEQ ID NO. 1–3. In particular embodiments, the DNA sequence is the same as or complementary to the base sequence of the entire coding region of a bacterial gene selected from the group of genes corresponding to SEQ ID NO. 1–3. Such an embodiment may, in addition, contain the control and regulatory sequence associated with the coding sequence.

The term, "DNA molecule", should be understood to refer to a linear polymer of deoxyribonucleotides, as well as to the linear polymer, base-paired with its complementary strand, forming double-strand DNA (dsDNA). The term is used as equivalent to "DNA chain" or "a DNA" or "DNA polymer" or "DNA sequence", so this description of the term meaning applies to those terms also. The term does not necessarily imply that the specified "DNA molecule" is a discrete entity with no bonding with other entities. The specified DNA molecule may have H-bonding interactions with other DNA molecules, as well as a variety of interactions with other molecules, including RNA molecules. In addition, the specified DNA molecule may be covalently linked in a longer DNA chain at one, or both ends. Any such DNA molecule can be identified in a variety of ways, including, by its particular nucleotide sequence, by its ability to base pair under stringent conditions with another DNA or RNA molecule having a specified sequence, or by a method of isolation which includes hybridization under stringent conditions with another DNA or RNA molecule having a specified sequence.

References to a "portion" of a DNA or RNA chain mean a linear chain which has a nucleotide sequence which is the same as a sequential subset of the sequence of the chain to which the portion refers. Such a subset may contain all of the sequence of the primary chain or may contain only a shorter sequence. The subset will contain at least 15 bases in a single strand.

However, by "same" is meant "substantially the same"; deletions, additions, or substitutions of specific nucleotides of the sequence, or a combination of these changes, which affect a small percentage of the full sequence will still leave the sequences substantially the same. Preferably this percentage of change will be less than 20%, more preferably less than 10%, and even more preferably less than 3%. "Same" is therefore distinguished from "identical"; for identical sequences there are no differences in nucleotide sequences.

As used in reference to nucleotide sequences, "complementary" has its usual meaning from molecular biology. Two nucleotide sequences or strands are complementary if they have sequences which would allow base pairing between the strands according to the usual pairing rules. This does not require that the strands would necessarily base pair at every nucleotide; two sequences can still be complementary with a low level of base mismatch such as that created by deletion, addition, or substitution of one or a few (up to 5 in a linear chain of 25 bases) nucleotides, or a combination of such changes.

A "coding sequence" or "coding region" refers to an open reading frame (ORF) which has a base sequence which is normally transcribed in a cell (e.g., a bacterial cell) to form RNA, which in most cases is translated to form a polypeptide. For the genes for which the product is normally a polypeptide, the coding region is that portion which encodes the polypeptide, excluding the portions which encode control and regulatory sequences, such as stop codons and promoter sequences.

Use of the term "isolated" indicates that a naturally occurring material or organism (e.g., a DNA sequence) has been removed from its normal environment. Thus, an isolated DNA sequence has been removed from its usual cellular environment, and may, for example, be in a cell-free solution or placed in a different cellular environment. For a molecule, such as a DNA sequence, the term does not imply that the molecule (sequence) is the only molecule of that type present.

It is also advantageous for some purposes that an organism or molecule (e.g., a nucleotide sequence) be in purified form. The term "purified" does not require absolute purity; instead, it indicates that the sequence, organism, or molecule is relatively purer than in the natural environment. Thus, the claimed DNA could not be obtained directly from total human DNA or from total human RNA. The claimed DNA sequences are not naturally occurring, but rather are obtained via manipulation of a partially purified naturally occurring substance (genomic DNA clones). The construction of a genomic library from chromosomal DNA involves the creation of vectors with genomic DNA inserts and pure individual clones carrying such vectors can be isolated from the library by clonal selection of the cells carrying the library.

In a further aspect, this invention provides an isolated or purified DNA sequence which is the same as or complementary to a bacterial gene homologous to one of the above-identified bacterial genes where the function of the expression product of the homologous gene is the same as the function of the product of one of the above-identified genes. In general, such a homologous gene will have a high level of nucleotide sequence similarity and, in addition, a protein product of homologous gene will have a significant level of amino acid sequence similarity. However, in addition, the product of the homologous gene has the same biological function as the product of the corresponding gene identified above.

In the context of the coding sequences and genes of this invention, "homologous" refers to genes whose expression results in expression products which have a combination of amino acid sequence similarity (or base sequence similarity for transcript products) and functional equivalence, and are therefore homologous genes. In general such genes also have a high level of DNA sequence similarity (i.e., greater than 80% when such sequences are identified among members of the same genus, but lower when these similarities are noted across bacterial genera), but are not identical. Relationships across bacterial genera between homologous genes are more easily identified at the polypeptide (i.e., the gene product) rather than the DNA level. The combination of functional equivalence and sequence similarity means that if one gene is useful, e.g., as a target for an antibacterial agent, or for screening for such agents, then the homologous gene is likewise useful. In addition, identification of one such gene serves to identify a homologous gene through the same relationships as indicated above. Typically, such homologous genes are found in other bacterial species, especially, but not restricted to, closely related species. Due to the DNA sequence similarity, homologous genes are often identified by hybridizing with probes from the initially identified gene under hybridizing conditions which allow stable S binding under appropriately stringent conditions (e.g., conditions which allow stable binding with approximately 85% sequence identity). The equivalent function of the product is then verified using appropriate biological and/or biochemical assays.

Similarly, the invention provides an isolated or purified DNA sequence which has a base sequence which is the same as the base sequence of a mutated bacterial gene selected from one of the genes identified in the first aspect where the expression of this DNA sequence or the mutated bacterial gene confers a growth conditional phenotype in the absence of expression of a gene which complements that mutation. Such an isolated or purified DNA sequence can have the base sequence which varies slightly from the base sequence of the original mutated gene but contains a base sequence change or changes which are functionally equivalent to the base sequence change or changes in the mutated gene. In most cases, this will mean that the DNA sequence has the identical bases at the site of the mutation as the mutated gene.

As indicated above, by providing the identified essential genes, the encoded expression products are also provided. Thus, another aspect concerns a purified, enriched, or isolated polypeptide, which is encoded by one of the identified essential genes. Such a polypeptide may include the entire gene product or only a portion or fragment of the encoded product. Such fragments are preferably biologically active fragments which retain one or more of the relevant biological activities of the full size gene product.

As is described below in the Detailed Description of the Preferred Embodiments, bacterial strains expressing a mutated form of one of the above identified genes, which confers a growth conditional phenotype, are useful for evaluating and characterizing the gene as an antibacterial target and for screening for antibacterial agents. Therefore, this invention also provides a purified bacterial strain expressing a mutated gene which is a mutated form of one of the bacterial genes identified above, where the mutated gene confers a growth conditional phenotype.

Similarly, this invention provides a recombinant bacterial cell containing an artificially inserted DNA construct which contains a DNA sequence which is the same as or complementary to one of the above-identified bacterial genes or a portion of one of those genes. Such cells are useful, for example, as sources of probe sequences or for providing a complementation standard for use in screening methods.

The term "recombinant bacterial cell" has its usual molecular biological meaning. The term refers to a microbe into which has been inserted, through the actions of a person, a DNA sequence or construct which was not previously found in that cell, or which has been inserted at a different location within the cell, or at a different location in the chromosome of that cell. Such a term does not include natural genetic exchange, such as conjugation between naturally occurring organisms. Thus, for example, a recombinant bacterium could have a DNA sequence inserted which was obtained from a different bacterial species, or may contain an inserted DNA sequence which is an altered form of a sequence normally found in that bacteria.

In a further aspect, this invention provides a method of diagnosing the presence of a bacterial strain having one of the genes identified above, by probing with an oligonucleotide at least 15 nucleotides in length, which specifically hybridizes to a nucleotide sequence which is the same as or complementary to the sequence of one of the bacterial genes identified above. In some cases, it is practical to detect the presence of a particular bacterial strain by direct hybridization of a labeled oligonucleotide to the particular gene. In other cases, it is preferable to first amplify the gene or a portion of the gene before hybridizing labeled oligonucleotides to those amplified copies. In particular embodiments, a longer oligonucleotide is used, for example, at least 20, 30, 50, or 100 nucleotides in length.

In a related aspect, this invention provides a method of diagnosing the presence of a bacterial strain by specifically detecting the presence of the transcriptional or translational product of the gene. Typically, a transcriptional (RNA) product is detected by hybridizing a labeled RNA or DNA probe to the transcript. Detection of a specific translational (protein) product can be performed by a variety of different tests depending on the specific protein product. Examples would be binding of the product by specific labeled antibodies and, in some cases, detection of a specific reaction involving the protein product.

As described above, the presence of a specific bacterial strain can be identified using oligonucleotide probes. Therefore this invention also provides such oligonucleotide probes at least 15 nucleotides in length, which specifically hybridize to a nucleotide sequence which is the same as or complementary to a portion of one of the bacterial chains identified above.

In a further related aspect, this invention provides a method of treating a bacterial infection in a mammal by administering a compound which is active against a bacterial gene selected from the group of genes corresponding to SEQ ID NO. 1–3, comprising espA and espB. In particular embodiments of this method, the infection involves a bacterial strain expressing a gene corresponding to one of the specified sequences, or a homologous gene. Such homologous genes provide equivalent biological function in other bacterial species.

"Treating", in this context, refers to administering a pharmaceutical composition for prophylactic and/or therapeutic purposes. The term "prophylactic treatment" refers to treating a patient who is not yet infected, but who is susceptible to, or otherwise at risk, of a particular infection. The term "therapeutic treatment" refers to administering treatment to a patient already suffering from an infection The term "bacterial infection" refers to the invasion of the host mammal by pathogenic bacteria. This includes the excessive growth of bacteria which are normally present in or on the body of a mammal. More generally, a bacterial infection can be any situation in which the presence of a bacterial population(s) is damaging to a host mammal. Thus, a mammal is "suffering" from a bacterial infection when excessive numbers of a bacterial population are present in or on a mammal's body, or when the effects of the presence of a bacterial population(s) is damaging the cells or other tissue of a mammal.

The term "administration" or "administering" refers to a method of giving a dosage of an antibacterial pharmaceutical composition to a mammal, where the method is, e.g., topical, oral, intravenous, transdermal, intraperitoneal, or intramuscular. The preferred method of administration can vary depending on various factors, e.g., the components of the pharmaceutical composition, the site of the potential or actual bacterial infection, the bacterium involved, and the severity of an actual bacterial infection.

The term "mammal" refers to any organism of the Class Mammalia of higher vertebrates that nourish their young with milk secreted by mammary glands, e.g., mouse, rat, and, in particular, human, dog, and cat.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In a related aspect, the invention provides a method for treating a bacterial infection in a mammal by administering an amount of an antibacterial agent effective to reduce the infection. The antibacterial agent specifically inhibits a biochemical pathway requiring the expression product of a gene corresponding to one of the genes identified in the first aspect above. Inhibition of that pathway inhibits the growth of the bacteria in vivo. In particular embodiments, the antibacterial agent inhibits the expression product of one of the identified genes.

In this context, the term "biochemical pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene.

In another related aspect, the invention provides a method of inhibiting the growth of a pathogenic bacterium by contacting the bacterium with an antibacterial agent which specifically inhibits a biochemical pathway requiring the expression product of a gene selected from the group of genes corresponding to SEQ ID NO. 1–3 or a homologous gene. Inhibition of that pathway inhibits growth of the bacterium. In particular embodiments, the antibacterial agent inhibits the expression product of one of the identified genes.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated.

A "pathogenic bacterium" includes any bacterium capable of infecting and damaging a mammalian host, and, in particular, includes *Staphylococcus aureus*. Thus, the term includes both virulent pathogens which, for example, can cause disease in a previously healthy host, and opportunistic pathogens which can only cause disease in a weakened or otherwise compromised host.

Similarly, the invention provides a method of prophylactic treatment of a mammal by administering a compound active against a gene selected from the group of genes corresponding to SEQ ID NO. 1–3 to a mammal at risk of a bacterial infection.

A mammal may be at risk of a bacterial infection, for example, if the mammal is more susceptible to infection or if the mammal is in an environment in which infection by one or more bacteria is more likely than in a normal setting. Therefore, such treatment can, for example, be appropriate for an immuno-compromised patient.

In a further related aspect a method of making an antibacterial agent is provided. The method involves screening for an agent active on one of the identified essential genes by providing a bacterial strain having a mutant form of one of the genes corresponding to SEQ ID NO. 1–3, or a homologous gene. As described above, the mutant form of the gene confers a growth conditional phenotype. A comparison bacterial strain is provided which has a normal form of said gene. The bacterial strains are contacted with a test compound in semi-permissive growth conditions, and the growth of the strains are compared to identify an antibacterial agent. The identified agent is synthesized in an amount sufficient to provide the agent in a therapeutically effective amount to a patient.

Further, in another aspect, this invention provides a pharmaceutical composition appropriate for use in the methods of treating bacterial infections described above, containing a compound active on a bacterial gene selected from the group of genes described above and a pharmaceutically acceptable carrier. Also, in a related aspect the invention provides a novel compound having antibacterial activity against one of the bacterial genes described above.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as peanut and sesame ails. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990) *Goodman and Gilman's: The Pharmacological Basis of Therapeutics*, 8th Ed., Pergamon Press.

Consistent with the usage of "antibacterial agent" herein, the term "antibacterial activity" indicates that the presence of a particular compound in the growth environment of a bacterial population reduces the growth rate of that population, without being a broad cellular toxin for other categories of cells.

Other features and advantages of the invention will be a p parent from the following description of the preferred embodiments, and from the claims.

BRIEF DESCRIPTION OF THE FIGURES

FIGS. 2A–1 to 2A–6 show the nucleotide sequence of the espAB operon (SEQ ID NOs. 1–3 along with the encoded amino acid sequences of EspA (SEQ ID NO. 4) and EspB (SEQ ID NO. 5).

FIG. 3 shows alignment of EspA sequence from *S. aureus* (Sau)(SEQ ID NO. 4) with the translated nucleotide sequences of genes having sequence similarity but of unknown function from *Bacillus subtilis* (Bsu) and *Streptococcus pyogenes* (Spy).

FIG. 4 shows a scheme for disrupting the espB gene.

FIG. 5 schematically illustrates the expected cellular localization of the espA and espB gene products.

FIG. 6 shows the percent inhibition of growth by a natural product extracts screening hit (HEPA screen) at a range of concentrations against 3 *S. aureus* strains, wild-type strain 8325-4, NT372 ts mutant, and the complemented ts mutant, SAM533.

DESCRIPTION OF THE PREFERRED EMBODIMENTS

Figure 1:
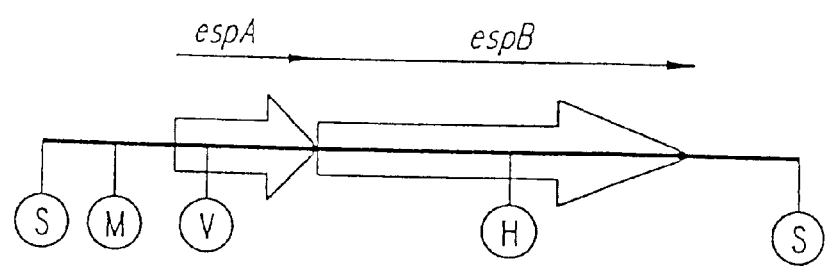
FIG. 1 shows a schematic map of the *Staphylococcus aureus* DNA insert contained within pMP373, showing the relative sizes, positions, and orientations of the espA and espB coding regions. Restriction sites are shown using the following abbreviations: M=Msp I; V=EcoR V; H=Hpa I; and S=Sau3A I.

I. General Approach for Identification of Target Genes

As was briefly described in the Summary above, this invention concerns essential genes in *Staphylococcus aureus*, in particular the operon containing the espA and espB coding sequences and the espA and EspB genes separately. This organism is a serious pathogen which frequently carries resistance to a variety of existing antibiotic agents. Such resistant strains of S. aureus are a particular problem in settings where antibacterial agents are intensively used, such as in hospitals. To overcome the therapeutic difficulties posed by the existing resistant strains, it is highly desirable that new classes of antibiotic drugs be found, particularly ones which are active against new bacterial targets. While such bacterial targets are usually (though not always) proteins, the targets can be identified by first identifying the bacterial genes which encode proteins (or RNA transcripts) that are essential for growth of the bacteria.

Identification of these genes, which are essential for growth of the bacteria, was accomplished by isolating conditional lethal mutant strains. Such mutant strains will grow under permissive conditions, but will not grow, or grow very poorly under non-permissive conditions. For the bacterial genes described herein, temperature sensitive mutants provided the growth conditional phenotype. The particular gene in each strain which was mutated to confer a growth conditional phenotype was then identified by isolating recombinant derivatives of the mutant strains. These recombinant strains each contained a DNA insert which, when expressed, would complement the defective gene and thus would allow growth under non-permissive conditions. These DNA inserts were provided by a genomic library of a normal S. aureus chromosome. The ability of the DNA insert in the recombinant strain to complement the defective product of the mutated gene showed that the DNA insert contained essentially a complete gene corresponding to a particular mutated gene. The vectors carrying each of these DNA inserts were constructed such that the S. aureus chromosomal insert could be amplified by PCR using flanking primer sequences. Each of the amplified S. aureus inserts was then sequenced, in general from both the 5' and 3' ends. The sequences described herein are believed to be correct, however, it is possible that the specified sequences may contain a low level of sequence errors compared to the actual gene sequence. However, any possible errors can be readily corrected by one skilled in the art by resequencing the gene using standard methods. In addition to the provision of a full sequence for the espA and espB coding regions, because partial sequences at the 5' and 3' ends bracket the complete gene, such partial sequences also uniquely identify and provide the complete gene without interference from a low level of sequencing error.

The complete gene and gene sequence can be reliably obtained by any of several different methods. For example, probes can be constructed based on the partial sequences provided, which can be used to probe genomic or cDNA libraries of S. aureus. Clones containing the corresponding 5' and 3' sequences can then be further characterized and sequenced to provide the complete gene. In another approach, the partial 5' and 3' sequences can be used to construct PCR primer sequences which can be used to amplify the sequence between those primers and likewise provide the complete gene. In yet another approach, equivalent growth conditional mutant strains can be obtained by following the same or a similar process of mutagenizing the base S. aureus strain, and then likewise obtaining the complete gene by isolating complementing clones which correspond to the sequences provided, from a genomic or cDNA library. It should again be noted that, for any of these approaches, a low level of sequencing error in the sequence presented herein does not matter, since the stringency of the hybridizing conditions can be readily adjusted to provide the appropriately specific binding. While the genes identified in this invention are highly useful as targets for novel antibacterial therapy, the genes and parts of those genes are also useful to provide probes which can be used to identify the presence of a particular bacteria carrying a particular gene. In addition, the growth conditional mutant strains described above are also useful as tools in methods for screening for antibacterial agents which target that gene (targeting the corresponding normal gene). The methods involved in the identification of the mutant strains complementing recombinant clones and the particular genes are described in more detail below.

A. Bacterial Strain Selection

The growth conditional mutant strains and recombinant strains herein are based on S. aureus strain 8325-4. This strain has been the subject of substantial genetic characterization and is appropriate for use in the approach described herein. It is believed to be free of transposons, phage or extrachromosomal elements. Numerous other strains of S. aureus can likewise be used. However, it is advantageous to select a strain which has few, or preferably no, transposons or extrachromosomal elements, as such elements can complicate the genetic analysis.

B. Isolation of Conditional Lethal Mutants (General).

Heat-sensitive mutants were obtained after diethyl sulfate (DES; SIGMA Chemical) mutagenesis of strain 8325-4. Briefly, single colonies were inoculated into LB broth in individual wells of a 96-well microtiter plate and grown overnight (35° C., 18 h). Culture supernatants (10 $\mu$l) were diluted into $\lambda$-dilution buffer ($\lambda$dil; 500 $\mu$l) and then treated with DES (5 $\mu$l). After a short incubation period (20 min at 37° C.), the treated cultures were serially diluted with $\lambda$dil into microtiter plates. After an additional incubation period (8–12 h. at 37° C.), appropriate dilutions (50 $\mu$l each of 10 E-2 and 10 E-3) were plated onto TS agar plates and incubated overnight (30° C., 18 h). The plates were replica-printed onto two Tryptic-soy (TS) plates and incubated either at 30° C. or 43° C. (permissive and non-permissive conditions, respectively). Colonies growing at 30° C. but not at 43° C. were isolated and their ts phenotype was subsequently confirmed in a second round of plating. Only one ts mutant was picked from an original singe-colony culture to assure that the mutants isolated were independent from each other. Independently-derived colonies with the appropriate phenotype are identified by direct screening on rich solid media at a permissive temperature (30° C.), as it obviates selection of mutants deficient in metabolic pathways, such as aromatic amino acid biosynthesis. No penicillin enrichment is employed, as it would counterselect mutant strains that are strongly bactericidal at the non-permissive temperature. A preliminary collection of 100 independent condition-lethal mutants and 71 non-independent mutants was made. This collection has been supplemented with additional condition-lethal mutants.

C. Creation of the S. aureus Shuttle Library

The S. aureus strain used for the preparation of genomic DNA for library construction as well as for the generation of conditional-lethal (temperature sensitive) mutants described in this document is a derivative of NCTC 8325, designated as 8325-4 (Novick, R. P., 1990). The 8325 parent strain is one of the better-characterized strains of S. aureus, with genetic and physical map data available in the current literature (Pattee, P. A., 1990). The 8325-4 derivative strain has all the chromosomal elements of the parent, with the exception of integrated (i.e., prophage and transposon DNA) and extrachromosomal (i.e., plasmid DNA) elements endogenous to the parent.

Cloning and subcloning experiments utilized the commercially-available *E. coli* strains JM109 (Promega) and DH5alpha (GIBCO-BRL). All enzymes cited (i.e., restriction endonucleases, ligases and phosphatases) were obtained commercially (NEB, Promega). All DNA cloning and manipulations are described in the current literature (Sambrook, et al., 1989). Parent plasmids pE194 and pUC19 have been described previously (Horinouchi, S. et al., 1982; Yanisch-Perron, C. et al., 1985) Recombinant constructs for use in a *S. aureus* host were first electroporated (Gene Pulser, BioRad) into *S. aureus* strain RN4220 (a restriction-deficient but methylase-proficient strain; Novick, R. P., 1990) before transduction into the target strain for complementation and cross-complementation analyses.

D. Library Construction

The shuttle plasmid vector used was pMP16, constructed by cloning the entire length of the natural *S. aureus* plasmid pE194 (linearized with Cla I) into the Nar I site of pUC19 (Yanisch-Perron et al., 1985). This new construct replicates and offers antibiotic resistance selections in both *E. coli* and *S. aureus*. It also provides blue-white screening to facilitate scoring of insert-containing clones. Carefully purified genomic DNA from *S. aureus* strain 8325-4 was partially digested (Sau3A I) and fragments of 2–8 kb were isolated by sucrose gradient centrifugation. DNA fragments isolated in this manner were then used for constructing two different libraries. In library A, the DNA fragments were directly cloned into pMP16, which had been linearized (Bam HI) and dephosphorylated (CIP). The DNA mixture was ligated (T4 DNA ligase) and transformed into *E. coli* DH5alpha. Library A thus constructed contains about 60,000 independent clones, 60% of which have inserts. In constructing library B, the ends of the Sau3A I fragments were partially filled with dGTP and DATP, ligated with linearized (Sal I) pMP16 that was partially filled with dCTP and dTTP, and transformed into *E. coli*. The advantage of partially filling the ends is that DNAs with the same ends can no longer ligate to each other; the majority of the ligation occurs between the vector and inserts, significantly increasing the percentage of insert-containing clones. In addition, the chance that two unrelated insert fragment are fortuitously ligated in the same clone is greatly reduced by using this strategy. Library B consists of 50,000 independent clones with >98% containing inserts. Both library A and library B contain at least a 50-fold representation of the *S. aureus* genome.

Clones from the two libraries were pooled and plasmid DNA extracted. The DNAs were used to transform S. aureus strain RN4220. About 100,000 erythromycin resistant transformants were pooled and infected with bacteriophage φ11 at a multiplicity of infection (MOI) of 0.01 to generate phage lysates containing the shuttle library plasmids. The lysates were then used to introduce the shuttle plasmids into ts mutants by transduction to isolate complementing clones.

E. Mobilization of the Mutation to an Isogenic Wild-type

A Tn917 transposon-insertion library in *S. aureus* 8325-4 was generated following a procedure essentially as described in Camilli et al., 1990, *J. Bacteriol.* 172:3738–3744; briefly, 8325-4 (pLTV1) was grown at 30° C. overnight (18 h.) in TSB (2 mL) containing erythromycin (2 μg/mL) to post-exponential phase.

This Tn917 library lysate was used to transduce the NT372 mutant to a temperature-resistant phenotype; this mutant was innoculated into TSB (3 mL) and grown overnight (18 h.) at 30° C.; the lysate from the Tn917 insertion library was added to give an MOI of 0.1, along with a solution of CaCl$_2$ (100 μL; 50 mM) and enough TSB to give a final volume of 4 mL. The mixture was incubated (30° C.) with shaking (15 m.) to allow infection to proceed, and then one volume of an ice-cold solution of sodium citrate (20 mM) was added. The cells were collected by centrifugation (3,000×g, 10 m.); the supernatant was removed and then the pellet resuspended in a solution of cold sodium citrate (100 μL; 20 mM).

The cell suspension was plated on TSA containing erythromycin (2μg/mL), sodium citrate (500 μg/mL) and Oxyrase (1:50 v/v). The plates were incubated at 30° C. until colonies began to appear (48 h.); these colonies were reselected on TSA-erythromycin plates at 43° C. Transducing lysates were prepared from the newly temperature-resistant colonies and used to transduce the parent mutant to erythromycin resistance. Successful transductants were replica plated at 30° C. and 43° C. to establish genetic linkage. Transducing lysates were made from those colonies scored as temperature-sensitive and erythromycin-resistant; these lysates were used to transduce 8325-4 to temperature sensitivity.

F. Isolation of Complementing Clones (General)

The lysate from library B was first chosen for transduction of the ts mutants because of its higher insert frequency. The ts mutants were grown either in TS broth or on TS agar plates overnight (18 h). The cells were resuspended in TS broth containing CaCl$_2$ (5 mM) to an OD$_{600}$ between 2–3. The lysate from library B (10–50 μl) was added to the resuspended cells (2 ml) and incubated at 30° C. with slow shaking (20 m). Ice-cold sodium citrate (20 mM; 1 ml) was added and the culture was centrifuged to pellet the cells. After removing the supernatant, the pellet was resuspended in ice-cold sodium citrate (20 mM; 500 μl). A small aliquot (about 1/5000 of the total volume) was plated on a TSA-ery-citrate plate (TS agar containing 5 μg/ml erythromycin and 500 μg/ml sodium citrate) and incubated at 30° C. overnight (18 h). The total number of erythromycin-resistant transductants screened were estimated from this plate; at least 200,000 transductants were screened for each ts mutant to assure that the library population was well represented. The rest of the cells were plated onto the same selection media (3–5 plates), incubated at 30° C. for 5 h and then at 43° C. overnight (18 h). Individual colonies that appeared on the 43° C. plates were isolated and infected with φ11 to generate lysates.

G. Strategy for DNA Sequencing of Complementing Clones (General)

DNA sequence ladders were generated by thermocycle sequencing procedures based upon the use of fluorescent-labeled primers (one of T7, SP6, M13 forward and M13 reverse; ABI), a thermostable DNA polymerase (AmpliTaq; Perkin Elmer/ABI) and dideoxy terminator chemistry (Sanger, et al, 1977, *Proc. Natl. Acad. Sci. USA* 74:54463). Data were acquired on an ABI 373A automated DNA sequencer (ABI) and processed using the PRISM sequence analysis software (ABI). For the nucleotide sequences disclosed herein, three independently generated genomic amplicons from the NT372 mutant were sequenced in parallel and were compared to a sequence derived from the parent strain (8325-4) to differentiate genomic mutations from possible PCR-induced amplification errors. The nucleotide sequences disclosed herein represent the range of highest quality data acquired in multiple passes from both strands. The complete nucleotide sequence of the complementing clone, including the ORFs defining the EspA and EspB polypeptides, is presented in FIG. 2, along with the translated amino acids below each condon triplet. The genomic point mutation producing the ts lethal phenotype of mutant NT372 occurs at position 835 of SEQ. ID. NO. 1, changing a "G" to an "A", resulting in the predicted amino acid change at residue 63 from glutamic acid ("E") to lysine ("K"). This mutation occurs in a region highly conserved among known members of the response regulator family.

For the sequences identified herein as SEQ ID NO. 1–3, the sequences corresponding to each complementing clone identify and provide the coding sequence (gene) responsible for providing that complementation. Therefore, the sequences corresponding to each complementing clone correspond to a particular essential gene.

H. DNA Sequence Analysis of Complementing Clones Similarity Searching (General)

Sequence data were analyzed for similarity to existing publicly-available database entries both at the nucleic acid level and the (putative) polypeptide level; the current releases and daily cumulative updates of these databases are maintained at the NCBI and are freely accessible. The programs BLASTN (Altschul, et al., 1990, *J. Mol. Biol.* 215:403–410) and FASTA (Pearson, et al., 1988, *Proc. natl. Acad. Sci. USA* 85:2444–2448) were used to search the nucleic acid databases GenBank (Release 102.0) and EMBL (Rel. 51.0). Putative open reading frames were identified using the GeneMark program (Borodovsky et al., 1994, *Nucl. Acids Res.* 22:4756–4767) using a *S. aureus* matrix. The programs BLASTX and TFASTA were used to search the protein databases SwissProt (Rel. 34.0), PIR (Rel. 53.0) and GenPept (Rel 102.0). For reporting the results of the similarity searching below, the following abbreviations of bacterial species names are used:

Bsu=*Bacillus subtilis*

Sau=*Staphylococcus aureus*

Spy=*Streptococcus pyogenes*

I. DNA Sequence of Complementing Clones

Among the mutants identified using the above approach, the mutant NT372, was selected for further analysis as described below.

1. Phenotype of *S. aureus* mutant NT372:

Mutant NT372 was initially identified by its inability to survive a temperature shift to 43° C. on TSA plates for 2 hours. The ts phenotype is partially rescued at 43° C. by plating either on TSA plates supplemented with 1M NaCl or Oxyrase; subsequent reselection of the surviving colonies on TSA alone at 43° C. reconfirms the ts phenotype. The phenotype does not seem to be linked to carbon source.

It is relatively difficult to introduce any Tn917 chromosomal insertions via transduction of mutant NT372, when compared to a number of other essential gene mutants, either at a fully permissive temperature (30° C.) or at a nonpermissive temperature (43° C.). The only method by which erythromycin-resistant transductants were obtained was by plating in a reduced oxygen environment; under these conditions, a tight linkage between the ermC gene of Tn917 and the chromosomal mutation (>98% cotransduction) was observed. Mobilization of the ts lesion to the isogenic parent results in a similar ts-lethal phenotype, indicating that the primary mutation lies within 40 kb of the transducible Tn917 erythromycin resistance marker; in contrast to the transduction of NT372, transduction of 8325-4 to erythromycin resistance exhibits ca. 50% linkage with the ts mutation. Another observed difference between the NT372 parent and the newly-created SAM1010 mutant (8325-4, espA-1, ermC) is the difference in reversion rates to temperature insensitivity; mutant NT372 reverts to temperature insensitivity less frequently (4×10E-9) than does SAM1010 (1×10E-5), suggestive of the presence of a second mutation in the primary mutant.

2. Identification of the NT372 Complementing Clone:

Three genomic clones were identified as complementing the ts defect of mutant NT372: pMP372, pMP373, and pMP374. The DNA inserts contained within each of the three plasmids were sequenced on both strands. The shortest clone, pMP373, contains an insert of 3731 nucleotides and is shared in common among the three complementing plasmids; analysis of the nucleotide sequence data with GeneMark identifies two complete open reading frames. FIG. 1 schematically shows the relative position and orientation of the espA and espB ORFs.

The first open reading frame is preceeded by a Shine-Dalgarno sequence (AGAGG) and is believed to begin at the ATG codon at position 649, although it is also possible that the start codon could be located at the preceeding ATG at position 643. The first reading frame terminates with a TAG at position 1350, resulting in a putative polypeptide of 233 amino acids with a predicted molecular mass of 27,200 Da and an isoelectric point of 5.0. The second open reading frame begins with an ATG at position 1363, preceeded by a Shine-Dalgarno sequence(AGAGG), and ends with a TAA at position 3189, resulting in a putative polypeptide of 609 amino acids with a predicted molecular mass of 69,900 Da and an isoelectric point of 5.4. There is a third ORF predicted by GeneMark analysis; it is preceeded by a Shine-Dalgarno seqence (AGACGG) and begins with an ATG overlapping the predicted 3' terminus of the second ORF at 3182, extending past the end of the clone. Since this clone does not marker-rescue the NT372 mutant, nor does it apparently encode a complete message for this third ORF, the mutant is likely to be complemented only by either or both of the first two ORFs.

There are no apparent ORFs identified by GeneMark analysis of the 648 nucleotide region upstream of espA; closer inspection reveals a few small (putative) ORFs with no clearly identifiable RBS sequences. There are no significant repetitive sequences in this region, either direct or indirect. There is a putative transcriptional start site approximately 200 nt upstream of the espA ORF; it is preceeded by a −35 sequence (TTGTCA) and a −10 sequence (ACTAAT) which are close to the consensus sequences for those of the housekeeping genes of *B. subtilis* (TTGACA and TATAAT, respectively). The sequence of the pMP373 insert, bracketing the espAB operon is shown in FIG. 2 (including the sequences of SEQ ID NO. 1–3).

3. The espA ORF Encodes a Polypeptide of the Response Regulator Family:

Similarity searching with the first putative open reading frame, espA, reveals a high level of similarity to a number of response regulator proteins. The highest similarity observed is to an uncharacterized open reading frame designated as yycF (Ogasawara, et al., 1994, DNA Res. 1: 1–14) from *B. subtilis*, giving an overall similarity of 89% and 74%. identity. Extensive similiarities are also noted to the ResD (Sun, et al, 1996, *J. Bacteriol.* 178:1374–1385) and PhoP (Seki, et al., 1987, *J. Bacteriol.* 169: 213–2916) proteins from *B. subtlilis* and the DrrA protein from Thermotoga maritima (Lee, et al., 1996, *J. Bacteriol.* 178: 5579–5585), placing it in the OmpR-PhoB subfamily of response regulators. Further examination of EspA reveals conserved features characteristic of the response regulator family of proteins (Volz, 1993, *Biochemistry* 332:11741–11753); Asp-10 lies within the first predicted beta-sheet, Asp-53 lies within the third predicted beta-sheet, and Lys-102 lies near the fifth predicted beta-sheet. The structural alignments as shown in FIG. 3, which includes the putative amino acid sequence of EspA (SEQ. ID NO. 4), demonstrate the conserved regions. The amino acid sequence of EspA is also shown in FIG. 7.

4. The espB ORF Encodes a Polypeptide of the Histidine Protein Kinase Family:

Similarity searching with the second open reading frame, EspB, reveals significant similarity to a number of histidine protein kinases, the highest of which is to an open reading frame designated as yycG from the *B. subtilis* genome sequencing project (Ogasawara, et al., 1994, DNA Res. 1: 1–14), giving an overall similarity of 69% and 46% identity. Further significant similarities are noted to the ResE (Sun, et al, 1996, *J. Bacteriol.* 178:1374–1385) and PhoR (Seki, et al., 1987, *J. Bacteriol.* 169: 213–2916) histidine protein kinases from *B. subtilis*. Hydrophobicity analysis of the translated open reading frame predicts two strongly hydrophobic stretches in the N-terminal third of the polypeptide, suggesting two. membrane-spanning regions with an intervening cell surface loop that may define the sensory domain. The putative amino acid sequence of the EspB polypeptide is shown in FIG. 8 (SEQ. ID NO. 5).

From primary sequence analysis, the HPK sensor appears to have an extracellular domain, suggesting that the signal for this essential event is exogeneous.

Thus, espAB encodes a two-component systems, of a type which is often involved in the regulation of cellular functions in bacteria. Two-component systems use phosphorylation as a means of information transfer across the bacterial membrane. In a typical two-component system, environmental signals result in the autophosphorylation of a unique histidine residue in the sensor component of the system, designated the histidine protein kinase (HPK); the signal is further transmitted by a second phosphorylation reaction which transfers the phosphate from the HPK to a specific aspartic acid residue of the response element, designated the response regulator (RR). The activated response regulator in turn triggers the expression of an array of genes that cause the organism to express a phenotype compatible with the conditions of the growth environment. The expected cellular location of the two components is shown schematically in FIG. 5.

Figure 4:
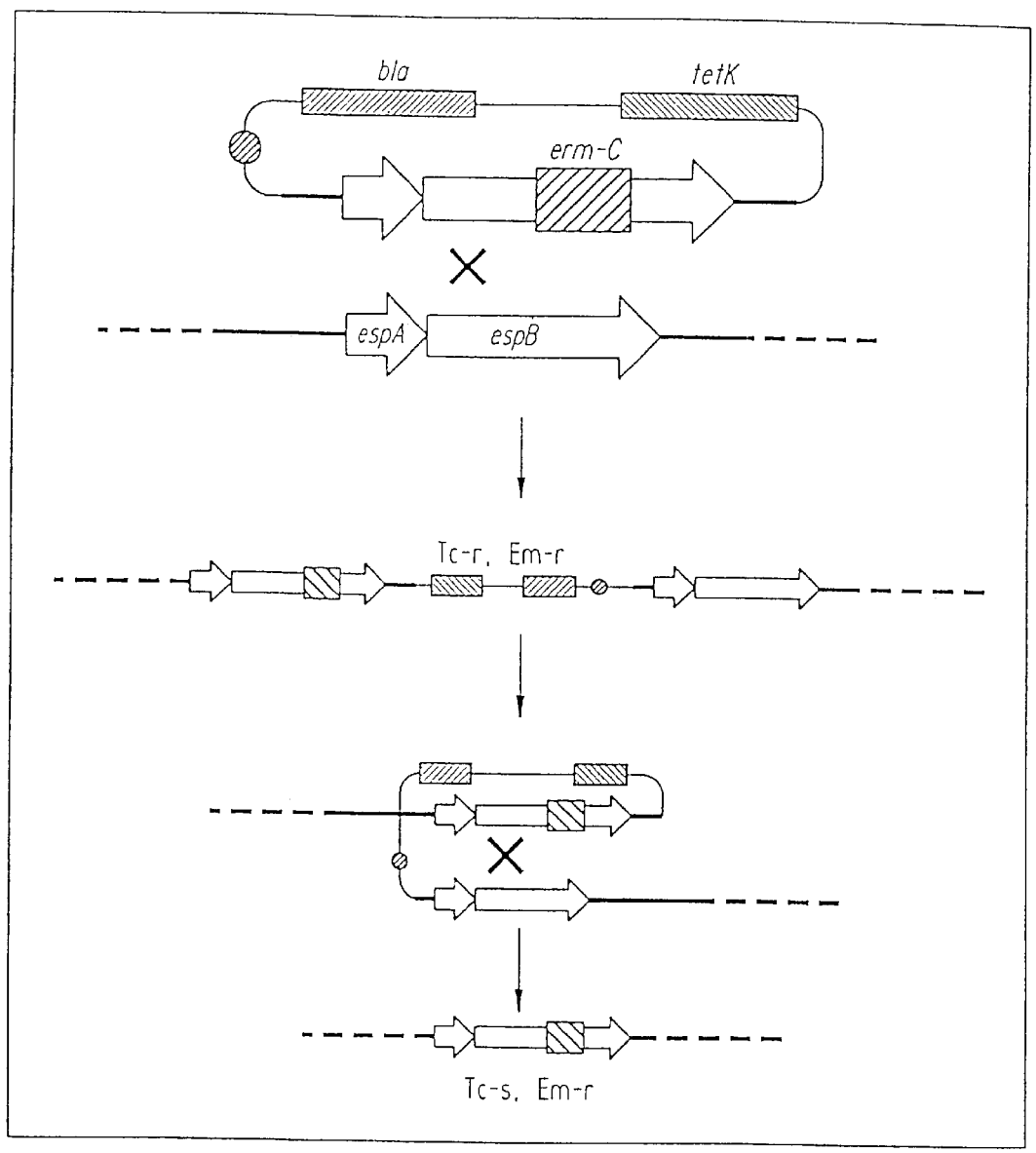

5. Both espA and espB Genes are Essential for Growth of *S. aureus*:

Two chromosomal integration constructs were created to achieve disruption of either the response regulator or the histidine protein kinase ORF; it is important to avoid the use of ts origins of replication in the integration constructs so that the gene in question can be demonstrated to be essential at all temperatures. The ermC gene from plasmid pE194 was inserted either at the EcoR V site to disrupt the EspA open reading frame (creating pMP626) at amino acid 53, or at the Hpa I site to disrupt the EspB open reading frame (creating pMP705) at amino acid 344. (The scheme is shown in FIG. 4.) Each of these constructs were integrated into the chromosome of RN4220, creating a tandem duplication consisting of a wild-type copy of the espAB locus and an additional copy of the locus with a disruption of either the espA or espB open reading frame. Integration of these constructs also adds another Sma I site; CHEF gel analysis of the Sma I genomic digests of each of the integrants indicates that the esp locus maps to fragment SmaI-F. These observations are confirmed by Southern blotting against the 8325-4 Sma I genomic digest.

Attempts to loop out the tandem duplication and retain the ermC disruption were successful only in the presence of a wild-type copy of the gene, borne on plasmid pMP621cat; this holds true for both the espA disruption, which is likely to be polar with respect to EspB, and the espB disruption.

Loop-out events were selected by the presence of erythromycin resistance and the loss of tetracycline resistance; these colonies were identified at 1 in 10,000, which contrasts with an observed loopout frequency of 1 in 500 for a non-essential gene. CHEF gel analysis of the Sma I digest of either genomic disruption demonstrates the loss of the extra restriction site introduced previously by the integration construct.

The nature of the constructs used in this work demonstrate that the presence of this signal transduction system is essential to the in vitro survival of *S. aureus*.

While many different cellular functions are regulated by two-component systems, most, if not all, appear to be involved in adaption to environmental changes and no HPK/RR system has been reported to be essential for survival of the bacterial cell. However, in the effort to define all in vitro essential genes of *S. aureus*, we identified a temperature-sensitive mutant, NT372, with a mutation in a locus bearing striking homology to known HPK genes. Subsequent cloning, DNA sequence analysis, and extensive genetic testing have demonstrated that the HPK/RR pair defined by the NT372 mutation contributes an essential function for *S. aureus* growth, as described above.

6. The expression of recombinant espA and espB genes

With the cloning and identification of espA and espB genes, it is routine for one skilled in the art to express recombinant espA and espB genes. These genes can be put under the control of a constitutive or inducible promoter in a suitable expression vector. These two genes can be either under the control of a single promoter, as in wild type *S. aureus* cells, or under the control of separate promoters. The vector can then be either transduced or electroporated into *S. aureus* cells, or other bacterial or non-bacterial cells. The vector should be selected to be compatible with the particular target cells. These two genes can be expressed simultaneously or separately in cells.

The expression of recombinant espA and espB genes in wild-type *S. aureus* cells can result in higher levels of corresponding polypeptides than in *S. aureus*. Since these two genes are essential for *S. aureus*, the overexpression of them may lead to special phenotypes of the cells. The phenotypes may then be used to study the functions of polypeptides encoded by these two genes.

The expression of espA and espB genes in *S. aureus* cells or other organism can be used to produce a large quantity of corresponding polypeptides, which thereby make it convenient to obtain isolated, purified, or enriched polypeptides. The polypeptides can then be used to study the biochemical and structural properties of espA and espB gene products. The understanding of these properties may facilitate the design of new drug to *S. aureus*. The polypeptides can also be used to raise the antibodies against espA and espB gene products.

Similarly, portions of either espA or EspB coding sequences can also be expressed as recombinant genes. Preferably, the portion encodes a corresponding polypeptide fragment with a length of at least 20 amino acid. The polypeptide fragments can be utilized in a similar way to corresponding full-length polypeptides.

II. Homologous Genes

As described above, the use of genes from other pathogenic bacterial strains and species which are homologous to the identified genes from *Staphylococcus aureus* is also provided. Such homologous genes not only have a high level of sequence similarity with these particular *S. aureus* genes, but also are functional equivalents. This indicates that the gene product has essentially the same biological activity. Therefore, the homologous genes are identifiable, for example, based on a combination of hybridization of all or a portion of one gene to the complement strand of its homologous counterpart, and the ability of the homologous gene to complement the growth conditional mutant of *S. aureus* under non-permissive conditions. The ability of the homologous gene to hybridize with sequences from the *S. aureus* gene provides that such a homologous gene can be readily obtained using generally accepted and used cloning techniques. The ability of the homologous gene to complement a defective *S. aureus* gene demonstrates that the genes are essentially equivalent genes found in different bacteria.

Specific examples of methods for identifying homologous genes are described in Van Dijl et al., U.S. Pat. No. 5,246,838, issued Sep. 21, 1993. In addition to the direct hybridization methods for identifying and isolating homologous genes mentioned above, Van Dijl et al. describe the isolation of homologous genes by isolating clones of a host bacterial strain which contain random DNA fragments from a donor microorganism. In those clones a specific host gene has been inactivated (such as by linkage with a regulatable promoter), and inserted homologous genes are identified by the complementation of the inactivated gene function. Homologous genes identified in this way can then be sequenced.

If the function of the product of a specific host gene is known, homologous gene products can often be isolated (by assaying for the appropriate activity) and at least partially sequenced (e.g., N-terminal sequencing). The amino acid sequence so obtained can then be used to deduce the degenerate DNA base sequence, which can be used to synthesize a probe(s) for the homologous gene. A DNA library from another microorganism is then probed to identify a clone(s) containing a homologous gene, and the clone insert sequenced.

These and other methods for identifying homologous genes are well-known to those skilled in the art. Therefore, other persons can readily obtain such genes which are homologous to the genes corresponding to SEQ ID NO. 1–3.

III. Evaluation of Gene as Therapeutic Target

A. General Considerations

While the identification of a particular bacterial gene as an essential gene for growth in a rich medium characterizes that gene as an antibacterial target, it is useful to characterize the gene further in order to prioritize the targets. This process is useful since it allows further work to be focused on those targets with the greatest therapeutic potential. Thus, target genes are prioritized according to which are more likely to allow identification of antibacterial agents which are:

1. Highly inhibitory to the target in relevant pathogenic species;
2. Cause rapid loss of bacterial viability;
3. Not have frequently arising resistance mechanisms;
4. Have high selectivity for the bacterial target and little, or preferably no, effect on the related mammalian targets;
5. Have low non-specific toxicity to mammals; and
6. Have appropriate pharmacodynamic and physical properties for use as a drug. Consequently, target genes are prioritized using a variety of methods, such as those described below.

B. Methods for Recognizing Good Targets

Essential genes can be characterized as either bactericidal or bacteriostatic. Earlier work with Salmonella mutants established that the bactericidal/bacteriostatic distinction was a characteristic of inhibition of the specific gene, rather than of a mutant allele, and could be characterized in vitro. (Schmid et al., 1989, *Genetics* 123:625–633.) Therefore, preferred targets (high priority) are those which are highly bactericidal when inhibited, causing cell death. A subset of the bactericidal essential genes can be identified as strongly bactericidal, resulting in rapid cell death when inhibited.

In *S. typhimurium*, inhibition of strongly bactericidal genes was shown to result in one of the following effects:

1. Cell lysis (such genes generally involved in cell wall biosynthesis);
2. Inhibition of protein synthesis;
3. DNA degradation; or
4. Entry into non-recoverable state involving cell cycle related genes.

C. In Vivo Evaluation of Microbial Virulence and Pathogenicity

In addition to the prioritization of gene targets based on the observed in vitro phenotypes, further evaluation of a specific gene as a potential therapeutic target is performed based on the effects observed with loss of that gene function in vivo. One approach is the use of null mutants in which the mutant gene product is inactive at 370° C. In the case of essential genes for which temperature sensitive mutants were previously isolated, those mutant strains can be used in this evaluation if the gene product is essentially inactive at 37° C. If such a temperature sensitive mutant has not previously been isolated but a complementing clone of some growth conditional mutant is available, then the required null mutants can generally be isolated through the use of localized mutagenesis techniques (Hong and Ames, 1971, *Proc. Natl. Acad. Sci. USA* 68:3158–3162). The evaluation then involves the comparison of the in vivo effects of the normal strain and the mutant strain. The comparison involves determinations of the relative growth in vivo, relative bactericidal phenotype in vivo and differences in response in various infection models.

Using gene target evaluation methods such as those described above, the identified target genes are evaluated in an infection model system. (References herein to the use of animals or mammals should be understood to refer to particular infection models. Other infection systems may be used, such as cell-based systems as surrogates for whole organism models, or systems to evaluate possible antimicrobial targets of pathogens of organisms other than animals (e.g., plants). The criteria for evaluation include the ability of the microbe to replicate, the ability to produce specific exoproducts involved in virulence of the organism, and the ability to cause symptoms of disease in the animals.

The infection models, e.g., animal infection models, are selected primarily on the basis of the ability of the model to mimic the natural pathogenic state of the pathogen in an organism to be treated and to distinguish the effects produced by activity or by loss of activity of a gene product (e.g., a switch in the expression state of the gene). Secondarily, the models are selected for efficiency, reproducibility, and cost containment. For mammal models, rodents, especially mice, rats, and rabbits, are generally the preferred species. Experimentalists have the greatest experience with these species. Manipulations are more convenient and the amount of materials which are required are relatively small due to the size of the rodents.

Each pathogenic microbe (e.g., bacterium) used in these methods will likely need to be examined using a variety of infection models in order to adequately understand the importance of the function of a particular target gene.

A number of animal models suitable for use with bacteria are described below. However, these models are only examples which are suitable for a variety of bacterial species; even for those bacterial species other models may be found to be superior, at least for some gene targets and possibly for all. In addition, modifications of these models, or perhaps completely different animal models are appropriate with certain bacteria.

Six animal models are currently used with bacteria to appreciate the effects of specific genes, and are briefly described below.

1. Mouse Soft Tissue Model

The mouse soft tissue infection model is a sensitive and effective method for measurement of bacterial proliferation. In these models (Vogelman et al., 1988, J. Infect. Dis. 157: 287–298) anesthetized mice are infected with the bacteria in the muscle of the hind thigh. The mice can be either chemically immune compromised (e.g., cytoxan treated at 125 mg/kg on days −4, −2, and 0) or immunocompetent. The dose of microbe necessary to cause an infection is variable and depends on the individual microbe, but commonly is on the order of $10^5$–$10^6$ colony forming units per injection for bacteria. A variety of mouse strains are useful in this model although Swiss Webster and DBA2 lines are most commonly used. Once infected the animals are conscious and show no overt ill effects of the infections for approximately 12 hours. After that time virulent strains cause swelling of the thigh muscle, and the animals can become bacteremic within approximately 24 hours. This model most effectively measures proliferation of the microbe, and this proliferation is measured by sacrifice of the infected animal and counting colonies from homogenized thighs.

2. Diffusion Chamber Model

A second model useful for assessing the virulence of microbes is the diffusion chamber model (Malouin et al., 1990, Infect. Immun. 58: 1247–1253; Doy et al., 1980, J. Infect. Dis. 2: 39–51; Kelly et al., 1989, Infect. Immun. 57: 344–350. In this model rodents have a diffusion chamber surgically placed in the peritoneal cavity. The chamber consists of a polypropylene cylinder with semipermeable membranes covering the chamber ends. Diffusion of peritoneal fluid into and out of the chamber provides nutrients for the microbes. The progression of the "infection" can be followed by examining growth, the exoproduct production or RNA messages. The time experiments are done by sampling multiple chambers.

3. Endocarditis Model

For bacteria, an important animal model effective in assessing pathogenicity and virulence is the endocarditis model (J. Santoro and M. E. Levinson, 1978, Infect. Immun. 19: 915–918). A rat endocarditis model can be used to assess colonization, virulence and proliferation.

4. Osteomyelitis Model

A fourth model useful in the evaluation of pathogenesis is the osteomyelitis model (Spagnolo et al., 1993, Infect. Immun. 61: 5225–5230). Rabbits are used for these experiments. Anesthetized animals have a small segment of the tibia removed and microorganisms are microinjected into the wound. The excised bone segment is replaced and the progression of the disease is monitored. Clinical signs, particularly inflammation and swelling are monitored. Termination of the experiment allows histolic and pathologic examination of the infection site to complement the assessment procedure.

5. Murine Septic Arthritis Model

A fifth model relevant to the study of microbial pathogenesis is a murine septic arthritis model (Abdelnour et al., 1993, Infect. Immun. 61: 3879–3885). In this model mice are infected intravenously and pathogenic organisms are found to cause inflammation in distal limb joints. Monitoring of the inflammation and comparison of inflammation vs. inocula allows assessment of the virulence of related strains.

6. Bacterial Peritonitis Model

Finally, bacterial peritonitis offers rapid and predictive data on the virulence of strains (M. G. Bergeron, 1978, Scand. J. Infect. Dis. Suppl. 14: 189–206; S. D. Davis, 1975, Antimicrob. Agents Chemother. 8: 50–53). Peritonitis in rodents, preferably mice, can provide essential data on the importance of targets. The end point may be lethality or clinical signs can be monitored. Variation in infection dose in comparison to outcome allows evaluation of the virulence of individual strains.

A variety of other in vivo models are available and may be used when appropriate for specific pathogens or specific genes. For example, target organ recovery assays (Gordee et al., 1984, *J. Antibiotics* 37:1054–1065; Bannatyne et al., 1992, Infect. 20:168–170) may be useful for fungi and for bacterial pathogens which are not acutely virulent to animals. For additional information the book by Zak and Sande (EXPERIMENTAL MODELS IN ANTIMICROBIAL CHEMOTHERAPY, 0. Zak and M. A. Sande (eds.), Academic Press, London (1986) is considered a standard.

It is also relevant to note that the species of animal used for an infection model, and the specific genetic make-up of that animal, may contribute to the effective evaluation of the effects of a particular gene. For example, immunoincompetent animals may, in some instances, be preferable to immuno-competent animals. For example, the action of a competent immune system may, to some degree, mask the effects of altering the level of activity of the test gene product as compared to a similar infection in an immunoincompetent animal. In addition, many opportunistic infections, in fact, occur in immuno-compromised patients, so modeling an infection in a similar immunological environment is appropriate.

In addition to these in vivo test systems, a variety of ex vivo models for assessing bacterial virulence may be employed (Falkow et al., 1992, *Ann. Rev. Cell Biol.* 8:333–363). These include, but are not limited to, assays which measure bacterial attachment to, and invasion of, tissue culture cell monolayers. With specific regard to *S. aureus*, it is well documented that this organism adheres to and invades cultured endothelial cell monolayers (Ogawa et al., 1985, Infect. Immun. 50: 218–224; Hamill et al., 1986, Infect. and Imm. 54:833–836) and that the cytotoxicity of ingested *S. aureus* is sensitive to the expression of known virulence factors (Vann and Proctor, 1988, Micro. Patho. 4:443–453). Such ex vivo models may afford more rapid and cost effective measurements of the efficacy of the experiments, and may be employed as preliminary analyses prior to testing in one or more of the animal models described above.

IV. Screening Methods for Antibacterial Agents

A. Use of Growth Conditional Mutant Strains Hypersensitivity and TS Mutant Phenoprints In addition to identifying new targets for drug discovery, the growth conditional mutants are useful for screening for inhibitors of the identified targets, even before the novel genes or biochemical targets are fully characterized. The methodology can be whole-cell based, is more sensitive than traditional screens searching for strict growth inhibitors, can be tuned to provide high target specificity, and can be structured so that more biological information on test compounds is available early for evaluation and relative prioritization of hits.

Certain of the screening methods are based on the hypersensitivity of growth conditional mutants. For example, conditionally lethal ts mutants having temperature sensitive essential gene functions are partially defective at a semipermissive temperature. As the growth temperature is raised, the mutated gene causes a progressively crippled cellular function. It is the inherent phenotypic properties of such ts mutants that are exploited for inhibitor screening.

Each temperature sensitive mutant has secondary phenotypes arising from the genetic and physiological effects of the defective cellular component. The genetic defect causes a partially functional protein that is more readily inhibited by drugs than the wild type protein. This specific hypersensitivity can be exploited for screening purposes by establishing "genetic potentiation" screens. In such screens, compounds are sought that cause growth inhibition of a mutant strain, but not of wild type, or greater inhibition of the growth of a mutant strain than of a wild type strain. Such compounds are often (or always) inhibitors of the wild type strain at higher concentrations.

Also, the primary genetic defect can cause far-reaching physiological changes in the mutant cells, even in semipermissive conditions. Necessity for full function of biochemically related proteins upstream and downstream of the primary target may arise. Such effects cause hypersensitivity to agents that inhibit these related proteins, in addition to agents that inhibit the genetically defective cellular component. The effects of the physiological imbalance will occur through metabolic interrelationships that can be referred to as the "metabolic web". Thus, in some cases, the initial genetic potentiation screen has the ability to identify inhibitors of either the primary target, or biochemically related essential gene targets.

B. Screening Strategy and Prototypes

1. Strain Validation and Screening Conditions

Hypersensitive strains (not growth conditional) have been successfully used in the past for discovery of new drugs targeting specific cellular pathways. (Kamogashira and Takegata, 1988, *J. Antibiotics* 41:803–10 806; Mumata et al., 1986, *J. Antibiotics* 39:994–1000.) The specific hypersensitivities displayed by ts-conditional mutants indicates that use of these mutants in whole cell screening provides a rapid method to develop target-specific screens for the identification of novel compounds. However, it is beneficial to eliminate mutants that will not be useful in semi-permissive growth conditions. Such mutant alleles may have nearly wild type function at the screening assay temperature. The simplest method for validating the use of ts mutants is to select those which show a reduced growth rate at the semi-restrictive growth temperature. A reduced growth rate indicates that the essential gene function is partially defective. More specific methods of characterizing the partial defect of a mutant strain are available by biochemical or physiological assays.

2. Multi-Channel Screening Approach

In addition to single strain screening, growth conditional mutants such as ts mutants, can be used in sets to provide compoud specific susceptibility profiles. As a screening tool, the mutant inhibition profile characterizes the effects of test compounds on specific bacterial pathways. Because the mutants are more sensitive than wild type strains, compounds with weak inhibition activity can be identified.

Such multi-channel screening can be performed as described in Boggs et al., SCREENING FOR MODULATORS OF BIOMOLECULES, U.S. application Ser. No. 08/589,257, filed Jan. 23, 1996, and International Publication No. WO96/23075, PCT/US96/00916, which are incorporated herein by reference including drawings. Growth conditional mutant strains having mutated forms of the genes described herein can beneficially be incorporated in a multi-channel screening panel.

3. Screening Method Refinement

Certain testing parameters for the genetic potentiation screening methods can significantly affect the identification of growth inhibitors, and thus can be manipulated to optimize screening efficiency and/or reliabilty. Notable among these factors are variable thermosensitivity of different ts mutants, increasing hypersensititivy with increasing temperature, and "apparent" increase in hypersensitivity with increasing compound concentration.

a. Variable Thermosensitivity

To use *S. aureus* ts mutants in genetic potentiation screening, the growth of these mutants at different temperatures should be measured to determine screening temperatures for each of these mutants. Different ts mutants have quite different maximum growth temperatures (MGT). Furthermore, different mutants that have mutations in the same gene may have quite different MGTs. Thus, different screening temperatures should be chosen for these mutants in order to accommodate the different growth preferences.

b. Raising screening Temperature Makes ts Mutants More Sensitive to Certain Compounds The ts mutants are more sensitive to potential inhibitors at elevated temperature. This temperature effect can be used to control hit rates in the screening. Higher screening temperature can be used to produce more hits for mutants that have low hit rates. Similarly, if a mutant shows a very high hit rate, the number of hits can be reduced by using lower screening temperatures to facilitate hit prioritization.

c. Increasing Compound Concentrations Affect Apparent Hypersensitivity

The concentration of compounds used in the screening is an important parameter in determining the hit rates and the amount of follow-up studies. The concentration of 10 $\mu$g/ml has been used in piloting screening studies. Screening at concentrations <2 $\mu$g/ml may miss at least half of the hits that would be identified at 10 $\mu$g/ml. On the other hand, screening at concentrations higher than 10 $\mu$g/ml may result in a large number of low quality hits and create too much work in hit confirmation and follow-up studies. At 10 $\mu$g/ml, a hit may appear as a growth inhibitor for both the mutant and wild type strains. This should not be a major problem since lower concentrations of the compound can be tested in the follow-up studies to differentiate its effect on the mutant and the wild type.

V. Description of Compound Screening Sources and Sub-structure Search Method

The methods of this invention are suitable and useful for screening a variety of sources for possible activity as inhibitors. For example, compound libraries can be screened, such as natural product libraries, combinatorial libraries, or other small molecule libraries. In addition, compounds from commercial sources can be tested, this testing is particularly appropriate for commercially available analogs of identified inhibitors of particular bacterial genes.

Compounds with identified structures from commercial sources can be efficiently screened for activity against a particular target by first restricting the compounds to be screened to those with preferred structural characteristics. As an example, compounds with structural characteristics causing high gross toxicity can be excluded. Similarly, once a number of inhibitors of a specific target have been found, a sub-library may be generated consisting of compounds which have structural features in common with the identified inhibitors. In order to expedite this effort, the ISIS computer program (MDL Information Systems, Inc.) is suitable to perform a 2D-substructure search of the Available Chemicals Directory database (MDL Information Systems, Inc.). This database contains structural and ordering information on approximately 175,000 commercially available chemical compounds. Other publicly accessible chemical databases may similarly be used.

VI. In vivo modeling: Gross Toxicity

Gross acute toxicity of an identified inhibitor of a specific gene target may be assessed in a mouse model. The inhibitor is administered at a range of doses, including high doses, (typically 0–100 mg/kg, but preferably to at least 100 times the expected therapeutic dose) subcutaneously or orally, as appropriate, to healthy mice. The mice are observed for 3–10 days. In the same way, a combination of such an inhibitor with any additional therapeutic components is tested for possible acute toxicity.

VII. Pharmaceutical Compositions and Modes of Administration

The particular compound that is an antibacterial agent can be administered to a patient either by itself, or in combination with another antibacterial agent, or in pharmaceutical compositions where it is mixed with suitable carriers or excipient(s). A combination of an inhibitor of a particular gene with another antibacterial agent can be of at least two different types. In one, a quantity of an inhibitor is combined with a quantity of the other antibacterial agent in a mixture, e.g., in a solution or powder mixture. In such mixtures, the relative quantities of the inhibitor and the other antibacterial agent may be varied as appropriate for the specific combination and expected treatment. In a second type of combination an inhibitor and another antibacterial agent can be covalently linked in such manner that the linked molecule can be cleaved within the cell. However, the term "in combination" can also refer to other possibilities, including serial administration of an inhibitor and another antibacterial agent. In addition, an inhibitor and/or another antibacterial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an EspA/EspB inhibitor should be in the range of 0.1–100 µg/ml.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture Such information can be used to more accurately determine useful doses in humans. Levels in plasma may be measured, for example, by HPLC.

The exact formulation, route of administration and dosage can be chosen by the individual physician in view of the patient's condition. (See, e.g., Fingl et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropyl-methyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

VIII. Use of Gene Sequences as Probes and Primers

In addition to the use of the growth conditional mutant strains as described above, DNA sequences derived from the identified genes are also useful as probes to identify the presence of bacteria having the particular gene or, under suitable conditions, a homologous gene. Similarly, such probes are useful as reagents to identify DNA chains which contain a sequence corresponding to the probe, such as for identifying clones having a recombinant DNA insert (such as in a plasmid). For identifying the presence of a particular DNA sequence or bacterium having that sequence it is preferable that a probe is used which will uniquely hybridize with that sequence. This can be accomplished, for example, by selecting probe sequences from variable regions, using hybridization conditions of suitably high stringency, and using a sufficiently long probe (but still short enough for convenient preparation and manipulation. Preferably, such probes are greater than 10 nucleotides in length, and more preferably greater than 15 nucleotides in length. In some cases, it is preferable that a probe be greater than 25 nucleotides in length. Those skilled in the art understand how to select the length and sequence of such probes to achieve specific hybridization. In addition, probes based on the specific genes and sequences identified herein can be used to identify the presence of homologous sequences (from homologous genes). For such purposes it is preferable to select probe sequences from portions of the gene which are not highly variable between homologous genes. In addition, the stringency of the hybridization conditions can be reduced to allow a low level of base mismatch.

As mentioned above, similar sequences are also useful as primers for PCR. Such primers are useful as reagents to amplify the number of copies of one of the identified genes or of a homologous gene. As with probes, it is preferable that the primers specifically hybridize with the corresponding sequence associated with one of the genes corresponding to SEQ ID NO. 1–3. Those skilled in the art understand how to select and utilize such primers.

Example 1: HEPA Screening with espAB ts Mutant

Figure 5:
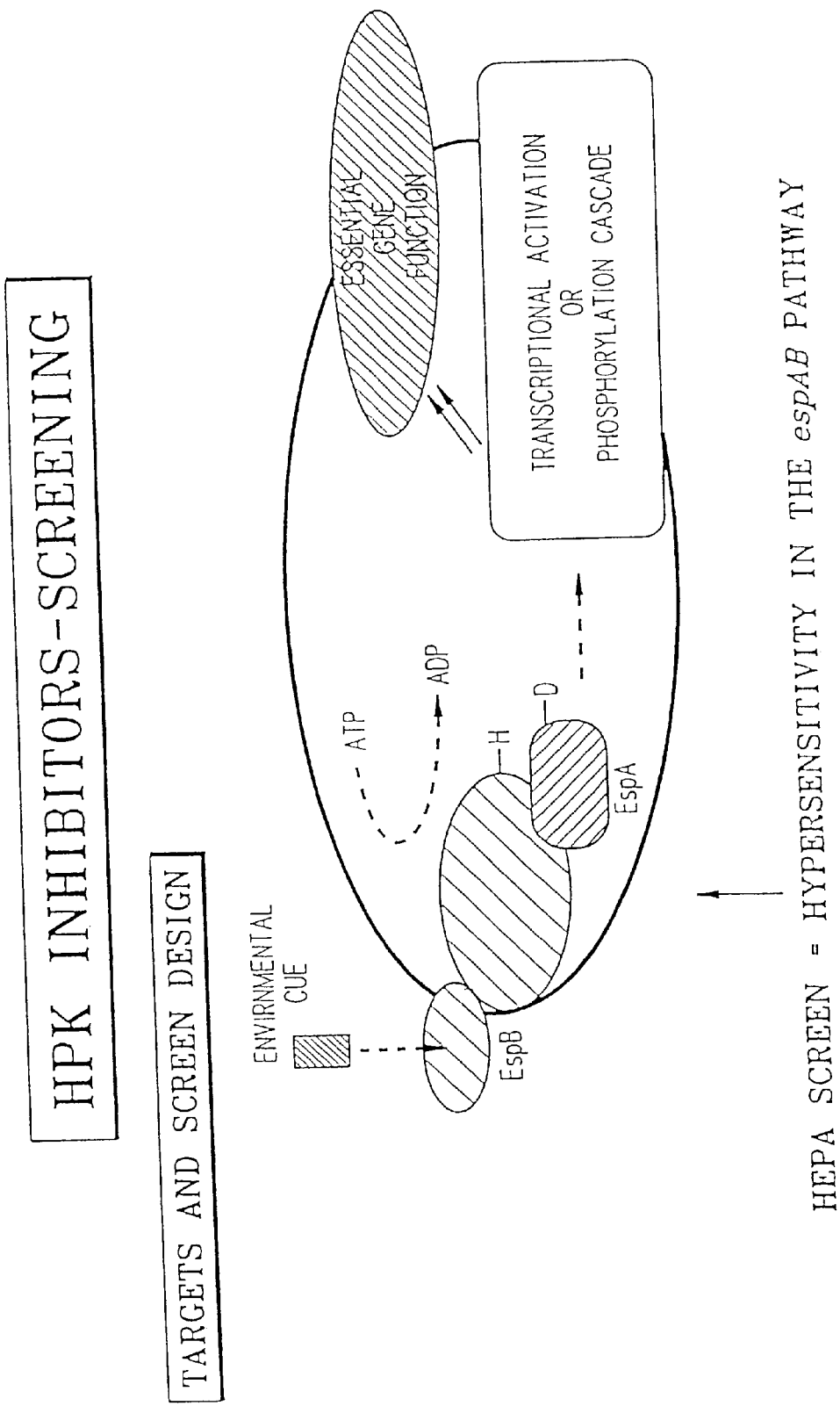

The essential sensor pair espAB is used as the target of the HEPA screen (hypersensitivity in the espAB pathway), which is designated to detect inhibitors of EspA and/or EspB function. The expected cellular location and general function of EspA and B is shown in FIG. 5, indicating that the EspB product is believed to locate to the cell membrane. The HEPA screen is a genetic potentiation screen and is summarized in the following.

A. HEPA screen: Initial Identification of Inhibitors

NT372 cells and isogenic wild type parent cells (8325-4) are grown overnight on TSA plates at 30° C. to isolate single colonies. A single colony of each cell type is recovered from the plates and inoculated into 3 ml of Mueller-Hinton (MH) broth. While these cells are incubating, screening plates are prepared by adding 40 $\mu$l of MH broth into each well of 96-well microtiter plates; test compounds are then added to the screening plates to achieve a 4 $\mu$g/ml screening concentration for synthetic compounds or a 1:1000 dilution of a stock extract for natural products screening. When the OD600 of the cell cultures reaches 0.2–0.3, the cells are diluted 1:1000 with MH broth and 50 $\mu$l added to wells in the screening plates. Blank wells and untreated controls for NT372 and WT are included in all screening plates. The inoculated screening plates are moved to a 37° C. incubator and allowed to incubate for 20 hours. This incubation temperature represents a maximum growth temperature for the NT372 mutant. Cells growing at this temperature have reduced amounts of functional EspAB and so are sensitive to compounds that specifically target the EspA and EspB proteins.

Hit-compounds were defined by the relative percentage of growth inhibition of NT372 and isogenic wild type cells when both cell types are exposed to a given test compound. Percent inhibition for each strain is calculated as: [1-(OD600 cpd well—OD600 blank well)/(OD600 no cpd well—OD600 blank well]× 100. In screening synthetic compounds, hits are defined as those compounds that inhibit the growth of NT372 ≧70% and WT cells <90%. In screening natural products, hits are defined as class AA (%Inh$_{NT372}$≧70% and %Inh$_{NT372}$—%Inh$_{wt}$≧90)or class A (%Inh$_{NT372}$≧70% and %Inh$_{NT372}$—%Inh$_{wt}$≧70).

B. HEPA screen: hit Progression—(Genetic and Biochemical Filters)

Figure 6:
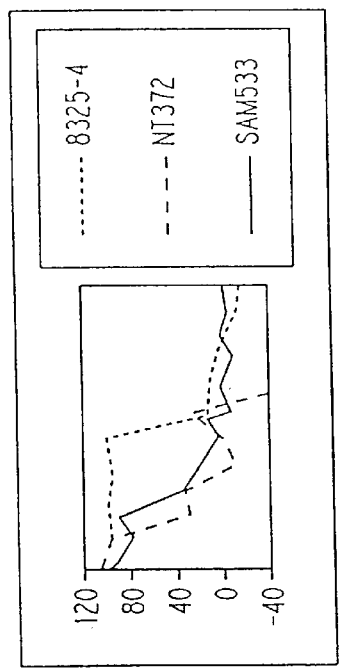

After initial identification of primary hits using the HEPA screen, confirmation and validation assays can be run to ensure the accuracy of the hits. Both assays are accommodated by the specificity-titration assay. This assay provides a comparative analysis of the activity of a hit in a titration series (128 µg/ml to 0.03 µg/ml) against WT, NT372, and the complemented NT372 mutant, SAM533. Strain SAM533 reverses the NT372 mutant phenotype, because it contains a plasmid encoding wild type espAB; thus, compounds that specifically target EspAB are not active against SAM533 as hypersensitivity to the hit-compound is eliminated by restoring normal levels of EspAB to the cell. Synthetic compounds that have a WT and SAM533 MIC <32 µg/ml and a NT372 MIC <8 µg/ml are retained for further analysis. In a similar manner, natural product hits are examined in a titration series (2% to 0.0009%) using the same strains; extracts that show a four-fold difference in sensitivity to WT/SAM533 and NT372 are retained for further examination. An example of the titration series validation of a HEPA screen natural products hit is shown in FIG. 6.

Hit evaluation can be extended through the use of biochemical assays to determine if hit compounds specifically affect the functioning of purified EspA and EspB components. The companion in vitro biochemical screen is set up using purified EspA and EspB proteins, which can be achieved expressing the espAB gene sequences. Leads identified from the specificity-titration assay will be examined for acceptable chemical structure, then utilized for analysis in the EspAB biochemical assay. This strategy for Stage I combines the powerful screening ability of a genetic-based search for EspAB inhibitors with a direct demonstration of EspAB targeting using the purified proteins.

C. HEPA Screening: Results (Synthetic and Natural Product Libraries)

Using the HEPA assay, synthetic compound and natural product extract were examined in pilot screens. The synthetics pilot comprised 11,200 compounds with a hit rate of 0.43% (8 hits total). The natural products pilot examined 4,800 extracts and identified 31 class AA and class A hits (0.65% hit rate).

These results demonstrate that the espAB pathway provides a useful screen to identify compounds having targeted antibacterial activity.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The nucleic acid and polypeptide sequences, pharmaceutical compositions, and methods described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds active on the identified genes or gene products, different nucleic acid or polypeptide sequences, different growth conditional mutants of the identified genes, and different recombinant constructs, as well as genes homologous to the specifically identified genes.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What is claimed is:

1. An oligonucleotide probe at least 15 nucleotides in length which specifically hybridizes to a nucleotide sequence which is the same as or complementary to a DNA sequence selected from the group consisting of SEQ ID NO. 1–3.

2. A recombinant bacterial cell containing an artificially inserted DNA construct comprising a nucleotide base sequence which is the same as or complementary to a nucleotide base sequence of the coding region of a DNA sequence selected from the group consisting of SEQ ID NO. 1–3.

3. The oligonucleotide probe of claim 1, wherein said coding region comprises SEQ ID NO. 2.

4. The oligonucleotide probe of claim 1, wherein said coding region comprises SEQ ID NO. 3.

5. The recombinant bacterial cell of claim 2, wherein said coding region comprises SEQ ID NO. 2.

6. The recombinant bacterial cell of claim 2, wherein said coding region comprises SEQ ID NO. 3.

* * * * *

SEQUENCE LISTING

<160> NUMBER OF SEQ ID NOS: 5

<210> SEQ ID NO 1
<211> LENGTH: 3731
<212> TYPE: DNA
<213> ORGANISM: Staphylococcus aureus -continued

```
<400> SEQUENCE: 1
gatcgcgggt tcgattcccg tcgagaccgt acaaatgcct atccaagagg ataggcattt      60
ttttgcgttt aatattatat taataaaaga tatatgacg  aatgataatc atattgattt     120
atctgttcgt ccatttcttt taaaatgtat gaacctcaag taacttagtg gttggatatg     180
aaagataaac gtagacaata aaatctttat tagacgtaca aacatatgct actgtcaaca     240
tatttcttcg ttgtgatatg ccaccagtcc tccataacat caattgttaa agtaacgaat     300
aacgaataat gatatttatt ttctgagcaa tgacgtgcaa ctagaagttg ccattatcct     360
aattttatta ttggaataga gacctcatca ttgtgttaaa tatcattgtc acaatccgcc     420
gtgagaaact aataaaaaat agtaatatat aagtttatat tggaaaatag aattaatagc     480
ttataaatgg taaattatat aataggttac tatacgttat aagacggaaa atgcgcacaa     540
taacaaaaat agtaagcgac atcctgtgat ttttacaca  aacataaacg ataaagaaca     600
aaaaatgata aaataatatt aatgatttaa gaaagaggt  ttatgcaaat ggctagaaaa     660
gttgttgtag ttgatgatga aaaaccgatt gctgatattt tagaatttaa cttaaaaaaa     720
gaaggatacg atgtgtactg tgcatacgat ggtaatgatg cagtcgactt aatttatgaa     780
gaagaaccag acatcgtatt actagatatc atgttacctg gtcgtgatgg tatggaagta     840
tgtcgtgaag tgcgcaaaaa atacgaaatg ccaataataa tgcttactgc taaagattca     900
gaaattgata aagtgcttgg tttagaacta ggtgcagatg actatgtaac gaaaccgttt     960
agtacgcgtg aattaatcgc acgtgtgaaa gcgaacttac gtcgtcatta ctcacaacca    1020
gcacaagaca ctggaaatgt aacgaatgaa atcacaatta agatattgt  gatttatcca    1080
gacgcatatt ctattaaaaa acgtggcgaa gatattgaat aacacatcg  tgaatttgaa    1140
ttgttccatt atttatcaaa acatatggga caagtaatga cacgtgaaca tttattacaa    1200
acagtatggg gctatgatta ctttggcgat gtacgtacgg tcgatgtaac gattcgtcgt    1260
ttacgtgaaa agattgaaga tgatccgtca catcctgaat atattgtgac gcgtagaggc    1320
gttggatatt tcctccaaca acatgagtag aggtcgaaac gaatgaagtg gctaaaacaa    1380
ctacaatccc ttcatactaa acttgtaatt gtttatgtat tactgattat cattggtatg    1440
caaattatcg ggtatatttt tacaaataac cttgaaaaag agctgcttga taattttaag    1500
aagaatatta cgcagtacgc gaaacaatta gaaattagta ttgaaaaagt atatgacgaa    1560
aagggctccg taaatgcaca aaaagatatt caaaatttat taagtgagta tgccaaccgt    1620
caagaaattg gagaaattcg ttttatagat aaagaccaaa ttattattgc gacgacgaag    1680
cagtctaacc gtagtctaat caatcaaaaa gcgaatgata gttctgtcca aaaagcacta    1740
tcactaggac aatcaaacga tcatttaatt ttaaaagatt atggcggtgg taaggaccgt    1800
gtctgggtat ataatatccc agttaaagtc gataaaaagg taattggtaa tatttatatc    1860
gaatcaaaaa ttaatgacgt ttataaccaa ttaaataata taaatcaaat attcattgtt    1920
ggtacagcta tttcattatt aatcacagtc atcctaggat tctttatagc gcgaacgatt    1980
accaaaccaa tcaccgatat gcgtaaccag acggtcgaaa tgtccagagg taactatacg    2040
caacgtgtga agatttatgg taatgatgaa attggcgaat tagctttagc atttaataac    2100
ttgtctaaac gtgtacaaga agcgcaggct aatactgaaa gtgagaaacg tagactggac    2160
tcagttatca cccatatgag tgatggtatt attgcaacag accgccgtgg acgtattcgt    2220
atcgtcaatg atatggcact caagatgctt ggtatggcga aagaagacat catcggatat    2280
tacatgttaa gtgtattaag tcttgaagat gaatttaaac tggaagaaat tcaagagaat    2340
```

-continued

```
aatgatagtt tcttattaga tttaaatgaa gaagaaggtc taatcgcacg tgttaacttt    2400
agtacgattg tgcaggaaac aggatttgta actggttata tcgctgtgtt acatgacgta    2460
actgaacaac aacaagttga acgtgagcgt cgtgaatttg ttgccaatgt atcacatgag    2520
ttacgtacac ctttaacttc tatgaatagt tacattgaag cacttgaaga aggtgcatgg    2580
aaagatgagg aacttgcgcc acaattttta tctgttaccc gtgaagaaac agaacgaatg    2640
attcgactgg tcaatgactt gctacagtta tctaaaatgg ataatgagtc tgatcaaatc    2700
aacaaagaaa ttatcgactt taacatgttc attaataaaa ttattaatcg acatgaaatg    2760
tctgcgaaag atacaacatt tattcgagat attccgaaaa agacgatttt cacagaattt    2820
gatcctgata aaatgacgca agtatttgat aatgtcatta caaatgcgat gaaatattct    2880
agaggcgata acgtgtcga gttccacgtg aaacaaaatc cactttataa tcgaatgacg    2940
attcgtatta aagataatgg cattggtatt cctatcaata aagtcgataa gatattcgac    3000
cgattctatc gtgtagataa ggcacgtacg cgtaaaatgg gtggtactgg attaggacta    3060
gccatttcga aagagattgt ggaagcgcac aatggtcgta tttgggcaaa cagtgtagaa    3120
ggtcaaggta catctatctt tatcacactt ccatgtgaag tcattgaaga cggtgattgg    3180
gatgaataat aaggagcata ttaaatctgt cattttagca ctactcgtct tgatgagtgt    3240
cgtattgaca tatatggtat ggaactttc tcctgatatt gcaaatgtcg acaatacaga    3300
tagtaagaag agtgaaacga aacctttaac gacacctatg acagccaaaa tggatacaac    3360
tattacgcca tttcagatta ttcattcgaa aaatgatcat ccagaaggaa cgattgcgac    3420
ggtatctaat gtgaataaac tgacgaaacc tttgaaaaat aaagaagtga agtccgtgga    3480
acatgttcgt cgtgatcata acttgatgat tcctgatttg aacagtgatt ttatattatt    3540
cgattttacg tatgatttac cgttatcaac atatcttggt caagtactga acatgaatgc    3600
gaaagtacca aatcatttca atttcaatcg tttggtcata gatcttgatg ctgatgataa    3660
tatcgtgctt tatgctataa gcaaagatcg ccacgattac gtaaaattaa caactacaac    3720
gaaaaatgat c                                                        3731
```

<210> SEQ ID NO 2
<211> LENGTH: 702
<212> TYPE: DNA
<213> ORGANISM: Staphylococcus aureus

<400> SEQUENCE: 2

```
atggctagaa aagttgttgt agttgatgat gaaaaaccga ttgctgatat tttagaattt      60
aacttaaaaa aagaaggata cgatgtgtac tgtgcatacg atggtaatga tgcagtcgac     120
ttaatttatg aagaagaacc agacatcgta ttactagata tcatgttacc tggtcgtgat     180
ggtatggaag tatgtcgtga agtgcgcaaa aaatacgaaa tgccaataat aatgcttact     240
gctaaagatt cagaaattga taaagtgctt ggtttagaac taggtgcaga tgactatgta     300
acgaaaccgt ttagtacgcg tgaattaatc gcacgtgtga aagcgaactt acgtcgtcat     360
tactcacaac cagcacaaga cactggaaat gtaacgaatg aaatcacaat taagatatt     420 gtgatttatc cagacgcata ttctattaaa aacgtggcg aagatattga attaacacat     480
cgtgaatttg aattgttcca ttatttatca aaacatatgg acaagtaat gacacgtgaa     540 catttattac aaacagtatg gggctatgat tactttggcg atgtacgtac ggtcgatgta     600
acgattcgtc gtttacgtga aaagattgaa gatgatccgt cacatcctga atatattgtg     660
```

-continued acgcgtagag gcgttggata tttcctccaa caacatgagt ag         702

<210> SEQ ID NO 3
<211> LENGTH: 1827
<212> TYPE: DNA
<213> ORGANISM: Staphylococcus aureus

<400> SEQUENCE: 3

| | | | | | |
|---|---|---|---|---|---|
| atgaagtggc | taaaacaact | acaatccctt | catactaaac | ttgtaattgt | ttatgtatta | 60 |
| ctgattatca | ttggtatgca | aattatcggg | ttatatttta | caaataacct | tgaaaaagag | 120 |
| ctgcttgata | attttaagaa | gaatattacg | cagtacgcga | acaattaga | aattagtatt | 180 |
| gaaaaagtat | atgacgaaaa | gggctccgta | aatgcacaaa | aagatattca | aaatttatta | 240 |
| agtgagtatg | ccaaccgtca | agaaattgga | gaaattcgtt | ttatagataa | agaccaaatt | 300 |
| attattgcga | cgacgaagca | gtctaaccgt | agtctaatca | atcaaaaagc | gaatgatagt | 360 |
| tctgtccaaa | aagcactatc | actaggacaa | tcaaacgatc | atttaatttt | aaaagattat | 420 |
| ggcggtggta | aggaccgtgt | ctgggtatat | aatatcccag | ttaaagtcga | taaaaggta | 480 |
| attggtaata | tttatatcga | atcaaaaatt | aatgacgttt | ataaccaatt | aataatata | 540 |
| aatcaaatat | tcattgttgg | tacagctatt | tcattattaa | tcacagtcat | cctaggattc | 600 |
| tttatagcgc | gaacgattac | caaaccaatc | accgatatgc | gtaaccagac | ggtcgaaatg | 660 |
| tccagaggta | actatacgca | acgtgtgaag | atttatggta | atgatgaaat | tggcgaatta | 720 |
| gctttagcat | ttaataactt | gtctaaacgt | gtacaagaag | cgcaggctaa | tactgaaagt | 780 |
| gagaaacgta | gactggactc | agttatcacc | catatgagtg | atggtattat | tgcaacagac | 840 |
| cgccgtggac | gtattcgtat | cgtcaatgat | atggcactca | agatgcttgg | tatggcgaaa | 900 |
| gaagacatca | tcggatatta | catgttaagt | gtattaagtc | ttgaagatga | atttaaactg | 960 |
| gaagaaattc | aagagaataa | tgatagtttc | ttattagatt | taaatgaaga | agaaggtcta | 1020 |
| atcgcacgtg | ttaactttag | tacgattgtg | caggaaacag | gatttgtaac | tggttatatc | 1080 |
| gctgtgttac | atgacgtaac | tgaacaacaa | caagttgaac | gtgagcgtcg | tgaatttgtt | 1140 |
| gccaatgtat | cacatgagtt | acgtacacct | ttaacttcta | tgaatagtta | cattgaagca | 1200 |
| cttgaagaag | gtgcatggaa | agatgaggaa | cttgcgccac | aattttttatc | tgttacccgt | 1260 |
| gaagaaacag | aacgaatgat | tcgactggtc | aatgacttgc | tacagttatc | taaaatggat | 1320 |
| aatgagtctg | atcaaatcaa | caagaaaatt | atcgacttta | acatgttcat | taataaaatt | 1380 |
| attaatcgac | atgaaatgtc | tgcgaaagat | acaacattta | ttcgagatat | tccgaaaaag | 1440 |
| acgattttca | cagaatttga | tcctgataaa | atgacgcaag | tatttgataa | tgtcattaca | 1500 |
| aatgcgatga | atattctag | aggcgataaa | cgtgtcgagt | tccacgtgaa | acaaaatcca | 1560 |
| ctttataatc | gaatgacgat | tcgtattaaa | gataatggca | ttggtattcc | tatcaataaa | 1620 |
| gtcgataaga | tattcgaccg | attctatcgt | gtagataagg | cacgtacgcg | taaaatgggt | 1680 |
| ggtactggat | taggactagc | catttcgaaa | gagattgtgg | aagcgcacaa | tggtcgtatt | 1740 |
| tgggcaaaca | gtgtagaagg | tcaaggtaca | tctatctta | tcacacttcc | atgtgaagtc | 1800 |
| attgaagacg | gtgattggga | tgaataa | | | | 1827 |

<210> SEQ ID NO 4
<211> LENGTH: 233
<212> TYPE: PRT
<213> ORGANISM: Staphylococcus aureus

<400> SEQUENCE: 4

```
Met Ala Arg Lys Val Val Val Asp Asp Glu Lys Pro Ile Ala Asp
 1               5                  10                  15

Ile Leu Glu Phe Asn Leu Lys Lys Glu Gly Tyr Asp Val Tyr Cys Ala
                20                  25                  30

Tyr Asp Gly Asn Asp Ala Val Asp Leu Ile Tyr Glu Glu Pro Asp
                35                  40                  45

Ile Val Leu Leu Asp Ile Met Leu Pro Gly Arg Asp Gly Met Glu Val
     50                  55                  60

Cys Arg Glu Val Arg Lys Lys Tyr Glu Met Pro Ile Ile Met Leu Thr
 65                  70                  75                  80

Ala Lys Asp Ser Glu Ile Asp Lys Val Leu Gly Leu Glu Leu Gly Ala
                 85                  90                  95

Asp Asp Tyr Val Thr Lys Pro Phe Ser Thr Arg Glu Leu Ile Ala Arg
                100                 105                 110

Val Lys Ala Asn Leu Arg Arg His Tyr Ser Gln Pro Ala Gln Asp Thr
            115                 120                 125

Gly Asn Val Thr Asn Glu Ile Thr Ile Lys Asp Ile Val Ile Tyr Pro
    130                 135                 140

Asp Ala Tyr Ser Ile Lys Lys Arg Gly Glu Asp Ile Glu Leu Thr His
145                 150                 155                 160

Arg Glu Phe Glu Leu Phe His Tyr Leu Ser Lys His Met Gly Gln Val
                165                 170                 175

Met Thr Arg Glu His Leu Leu Gln Thr Val Trp Gly Tyr Asp Tyr Phe
                180                 185                 190

Gly Asp Val Arg Thr Val Asp Val Thr Ile Arg Arg Leu Arg Glu Lys
            195                 200                 205

Ile Glu Asp Asp Pro Ser His Pro Glu Tyr Ile Val Thr Arg Arg Gly
    210                 215                 220

Val Gly Tyr Phe Leu Gln Gln His Glu
225                 230

<210> SEQ ID NO 5
<211> LENGTH: 608
<212> TYPE: PRT
<213> ORGANISM: Staphylococcus aureus

<400> SEQUENCE: 5

Met Lys Trp Leu Lys Gln Leu Gln Ser Leu His Thr Lys Leu Val Ile
 1               5                  10                  15

Val Tyr Val Leu Leu Ile Ile Ile Gly Met Gln Ile Ile Gly Leu Tyr
                20                  25                  30

Phe Thr Asn Asn Leu Glu Lys Glu Leu Leu Asp Asn Phe Lys Lys Asn
                35                  40                  45

Ile Thr Gln Tyr Ala Lys Gln Leu Glu Ile Ser Ile Glu Lys Val Tyr
     50                  55                  60

Asp Glu Lys Gly Ser Val Asn Ala Gln Lys Asp Ile Gln Asn Leu Leu
 65                  70                  75                  80

Ser Glu Tyr Ala Asn Arg Gln Glu Ile Gly Glu Ile Arg Phe Ile Asp
                 85                  90                  95

Lys Asp Gln Ile Ile Ile Ala Thr Thr Lys Gln Ser Asn Arg Ser Leu
                100                 105                 110

Ile Asn Gln Lys Ala Asn Asp Ser Ser Val Gln Lys Ala Leu Ser Leu
            115                 120                 125

Gly Gln Ser Asn Asp His Leu Ile Leu Lys Asp Tyr Gly Gly Gly Lys
```

```
                    130                 135                 140
Asp Arg Val Trp Val Tyr Asn Ile Pro Val Lys Val Asp Lys Lys Val
145                 150                 155                 160

Ile Gly Asn Ile Tyr Ile Glu Ser Lys Ile Asn Asp Val Tyr Asn Gln
                    165                 170                 175

Leu Asn Asn Ile Asn Gln Ile Phe Ile Val Gly Thr Ala Ile Ser Leu
                180                 185                 190

Leu Ile Thr Val Ile Leu Gly Phe Phe Ile Ala Arg Thr Ile Thr Lys
            195                 200                 205

Pro Ile Thr Asp Met Arg Asn Gln Thr Val Glu Met Ser Arg Gly Asn
210                 215                 220

Tyr Thr Gln Arg Val Lys Ile Tyr Gly Asn Asp Glu Ile Gly Glu Leu
225                 230                 235                 240

Ala Leu Ala Phe Asn Asn Leu Ser Lys Arg Val Gln Glu Ala Gln Ala
                245                 250                 255

Asn Thr Glu Ser Glu Lys Arg Arg Leu Asp Ser Val Ile Thr His Met
                260                 265                 270

Ser Asp Gly Ile Ile Ala Thr Asp Arg Arg Gly Arg Ile Arg Ile Val
            275                 280                 285

Asn Asp Met Ala Leu Lys Met Leu Gly Met Ala Lys Glu Asp Ile Ile
290                 295                 300

Gly Tyr Tyr Met Leu Ser Val Leu Ser Leu Glu Asp Glu Phe Lys Leu
305                 310                 315                 320

Glu Glu Ile Gln Glu Asn Asn Asp Ser Phe Leu Leu Asp Leu Asn Glu
                325                 330                 335

Glu Glu Gly Leu Ile Ala Arg Val Asn Phe Ser Thr Ile Val Gln Glu
                340                 345                 350

Thr Gly Phe Val Thr Gly Tyr Ile Ala Val Leu His Asp Val Thr Glu
            355                 360                 365

Gln Gln Gln Val Glu Arg Glu Arg Arg Glu Phe Val Ala Asn Val Ser
        370                 375                 380

His Glu Leu Arg Thr Pro Leu Thr Ser Met Asn Ser Tyr Ile Glu Ala
385                 390                 395                 400

Leu Glu Glu Gly Ala Trp Lys Asp Glu Glu Leu Ala Pro Gln Phe Leu
                405                 410                 415

Ser Val Thr Arg Glu Glu Thr Glu Arg Met Ile Arg Leu Val Asn Asp
                420                 425                 430

Leu Leu Gln Leu Ser Lys Met Asp Asn Glu Ser Asp Gln Ile Asn Lys
            435                 440                 445

Glu Ile Ile Asp Phe Asn Met Phe Ile Asn Lys Ile Ile Asn Arg His
450                 455                 460

Glu Met Ser Ala Lys Asp Thr Thr Phe Ile Arg Asp Ile Pro Lys Lys
465                 470                 475                 480

Thr Ile Phe Thr Glu Phe Asp Pro Asp Lys Met Thr Gln Val Phe Asp
                485                 490                 495

Asn Val Ile Thr Asn Ala Met Lys Tyr Ser Arg Gly Asp Lys Arg Val
                500                 505                 510

Glu Phe His Val Lys Gln Asn Pro Leu Tyr Asn Arg Met Thr Ile Arg
            515                 520                 525

Ile Lys Asp Asn Gly Ile Gly Ile Pro Ile Asn Lys Val Asp Lys Ile
        530                 535                 540

Phe Asp Arg Phe Tyr Arg Val Asp Lys Ala Arg Thr Arg Lys Met Gly
545                 550                 555                 560
```

-continued

```
Gly Thr Gly Leu Gly Leu Ala Ile Ser Lys Glu Ile Val Glu Ala His
            565                 570                 575

Asn Gly Arg Ile Trp Ala Asn Ser Val Glu Gly Gln Gly Thr Ser Ile
            580                 585                 590

Phe Ile Thr Leu Pro Cys Glu Val Ile Glu Asp Gly Asp Trp Asp Glu
            595                 600                 605
```